(12) United States Patent
Stevenson et al.

(10) Patent No.: US 9,352,148 B2
(45) Date of Patent: May 31, 2016

(54) HEADER BLOCK FOR AN AIMD WITH AN ABANDONED LEAD CONNECTOR CAVITY

(71) Applicant: Greatbatch Ltd., Clarence, NY (US)

(72) Inventors: Robert A. Stevenson, Canyon Country, CA (US); Richard L. Brendel, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/192,835

(22) Filed: Feb. 27, 2014

(65) Prior Publication Data

US 2014/0243944 A1    Aug. 28, 2014

Related U.S. Application Data

(60) Provisional application No. 61/769,762, filed on Feb. 27, 2013.

(51) Int. Cl.
| | |
|---|---|
| *A61N 1/375* | (2006.01) |
| *A61N 1/08* | (2006.01) |
| A61N 1/37 | (2006.01) |
| H01R 103/00 | (2006.01) |
| H01R 24/58 | (2011.01) |

(52) U.S. Cl.
CPC ............. *A61N 1/08* (2013.01); *A61N 1/3752* (2013.01); *A61N 1/3718* (2013.01); *A61N 2001/086* (2013.01); *H01R 24/58* (2013.01); *H01R 2103/00* (2013.01); *H01R 2201/12* (2013.01)

(58) Field of Classification Search
CPC ..... A61N 1/08; A61N 1/3752; A61N 1/3718; A61N 2001/086; H01R 2201/12
See application file for complete search history.

(56) References Cited

U.S. PATENT DOCUMENTS

| | | |
|---|---|---|
| 7,225,034 B2 | 5/2007 | Ries et al. |
| 2004/0260373 A1 | 12/2004 | Ries et al. |
| 2010/0070009 A1 | 3/2010 | Barker |
| 2010/0137956 A1 | 6/2010 | Osypka |
| 2010/0174349 A1 | 7/2010 | Stevenson et al. |
| 2010/0324639 A1* | 12/2010 | Stevenson et al. ............ 607/116 |
| 2011/0029052 A1 | 2/2011 | McDonald et al. |
| 2013/0310900 A1 | 11/2013 | Cabunaru et al. |

OTHER PUBLICATIONS

EP Search, "12158362.9-2305", Jul. 5, 2012.
Extended Search, "12158362.9-1652", Jun. 5, 2013.

* cited by examiner

*Primary Examiner* — Tammie K Heller
(74) *Attorney, Agent, or Firm* — Marc G. Martino; Michael F. Scalise

(57) ABSTRACT

A header for an active implantable medical device includes a header block body and at least one active connector cavity configured to be attachable to an active lead. A first conductive leadwire has a first and second end, where the first end of the first conductive leadwire is electrically connected to the at least one active connector cavity and the second end of the first conductive leadwire is connectable to a hermetic terminal of the active implantable medical device. At least one abandoned connector cavity is located within the header block body configured to attachable to an abandoned lead. A second conductive leadwire has a first and second end, where the first end of the second conductive leadwire is electrically connected to the at least one abandoned connector cavity and the second end of the second conductive leadwire is connectable to the active implantable medical device housing.

21 Claims, 27 Drawing Sheets

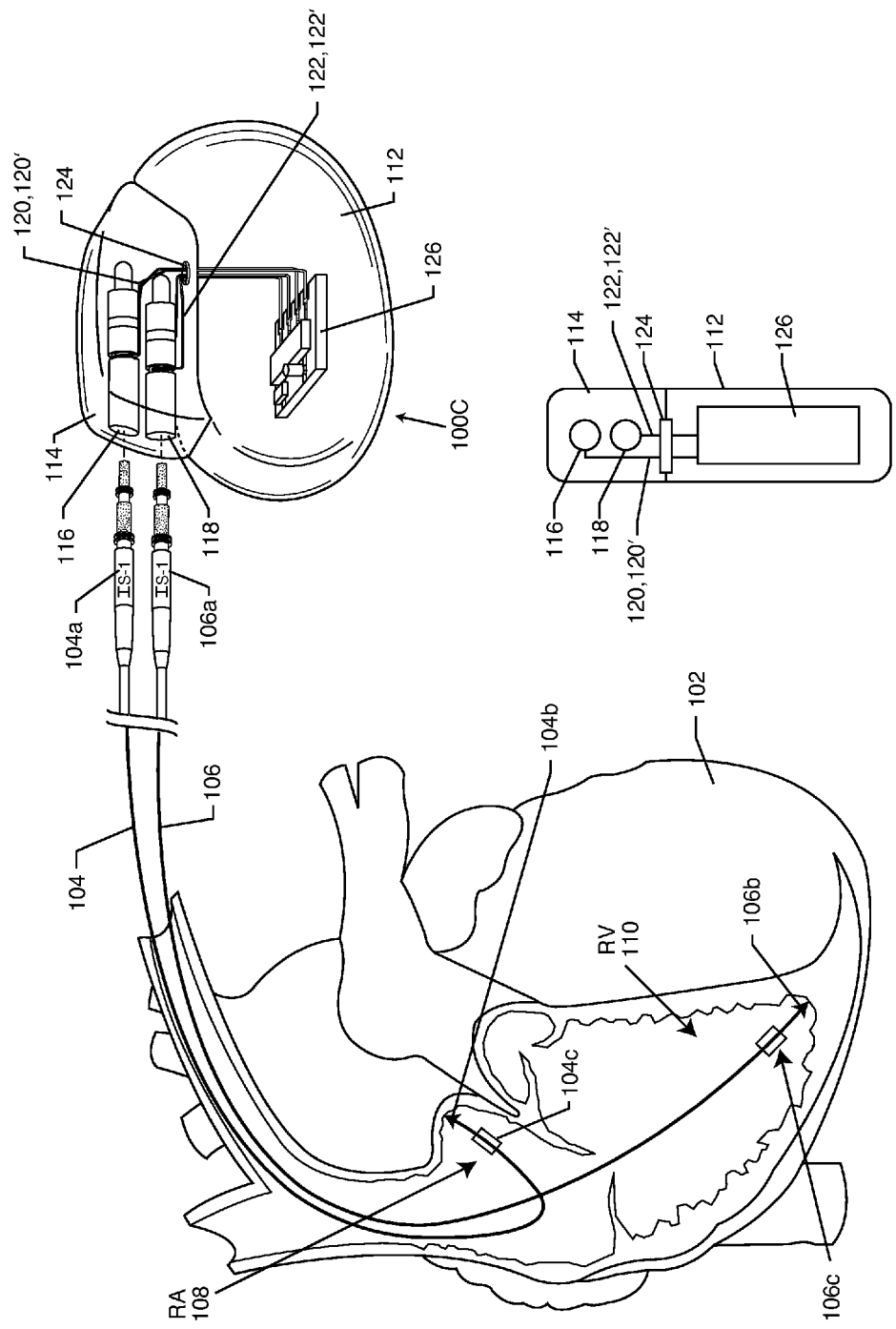

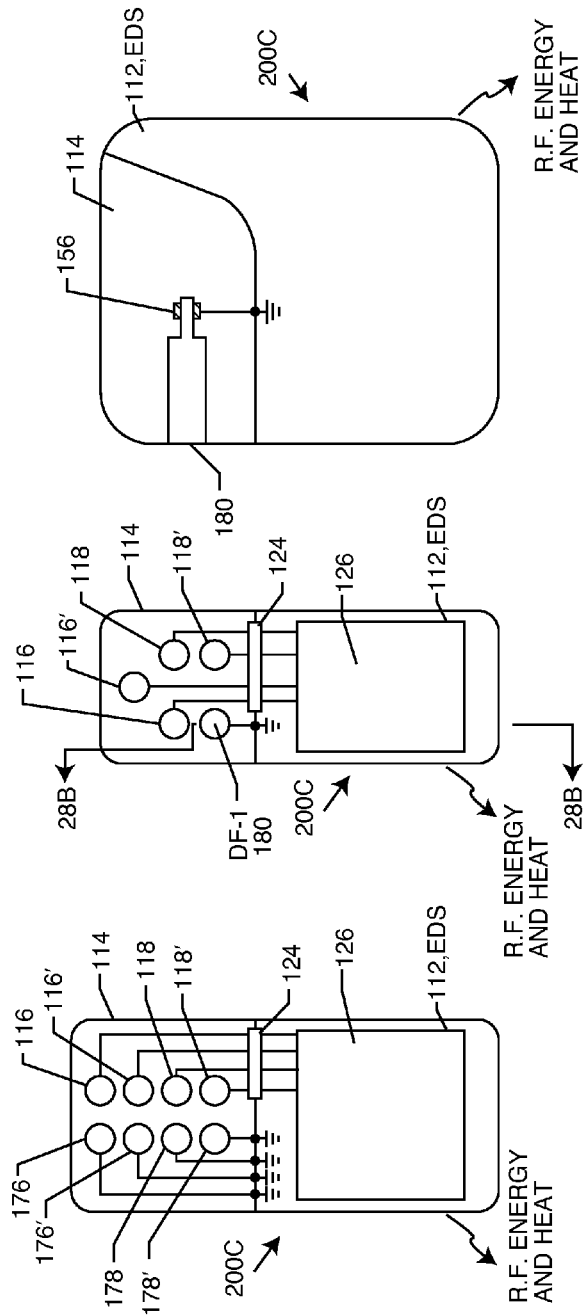

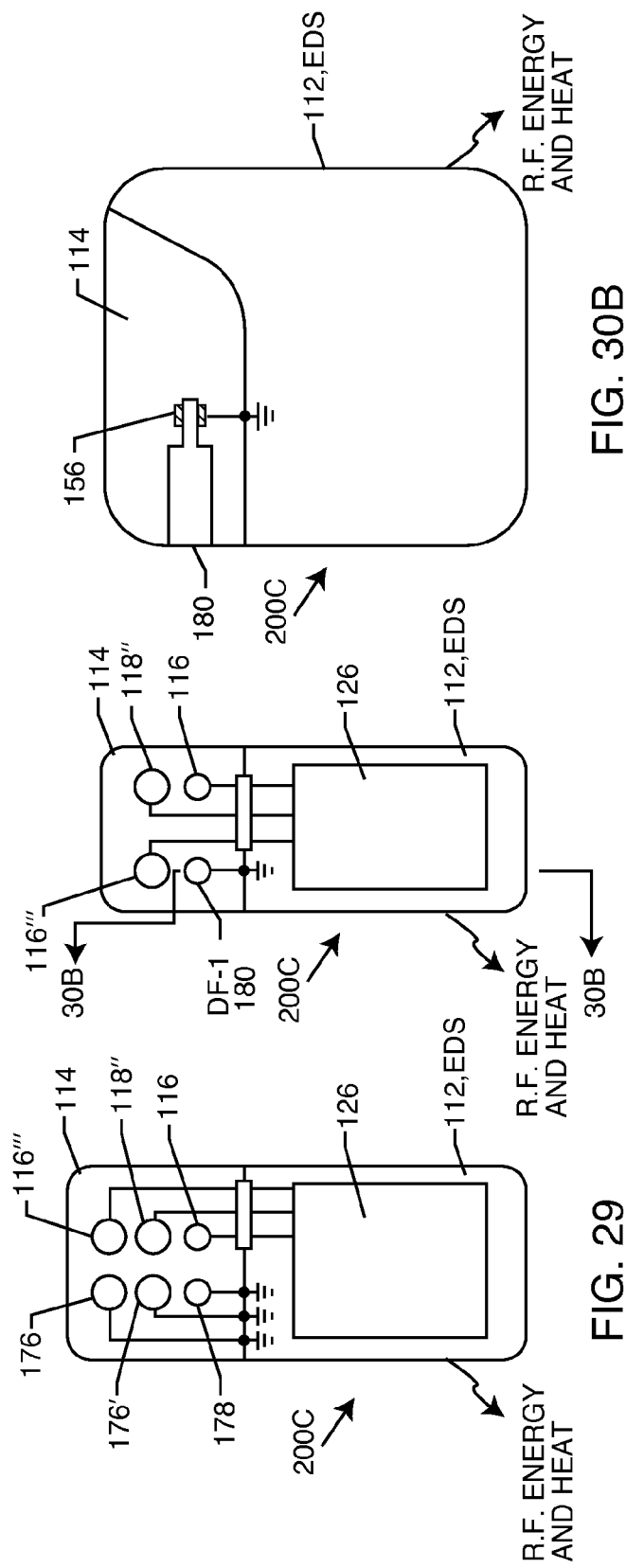

HEADER BLOCK FOR AN AIMD WITH AN ABANDONED LEAD CONNECTOR CAVITY

CROSS-REFERENCE TO RELATED APPLICATIONS

This non-provisional application claims priority to provisional application 61/769,762 filed on Feb. 27, 2013, the contents of which are fully incorporated herein with this reference.

FIELD OF THE INVENTION

The present invention generally relates to headers/header blocks for active implantable medical devices (AIMDs) such as, cardiac pacemakers, implantable cardioverter defibrillators (ICD), cardiac resynchronization therapy (CRT) devices, neurostimulators and related leads. More specifically, the present invention relates to a header/header block including at least one port for attachment of an abandoned lead.

BACKGROUND OF THE INVENTION

Transvenous cardiac pacemakers and ICDs using leads threaded into the right sided chambers of the heart through the venous system have evolved over the years from single chamber (one implanted lead) to dual chamber (two implanted leads); then to single and eventually dual chamber ICDs. More recently with the wider recognition of the increased incidence of heart failure secondary to right sided pacing of the heart, as well to numerous other etiologies, CRT devices have been developed with left sided chamber leads delivered transvenously to endocardial locations, and/or on through the coronary sinus to left ventricular epicardial locations, and/or with a variety of transthoracic approaches to direct epicardial or intramyocardial left ventricular or left atrial stimulation sites.

In a typical prior art dual chamber defibrillator system, there is a trifurcated ventricular lead connector, with one arm providing low voltage IS-1 pace-sense function and two arms providing high voltage DF-1 connections. An advantage of this configuration was that if one of the high voltage or low voltage components of this type of lead failed, it could be corrected relatively simply by implanting a replacement single function lead, disconnecting the failed component from the pulse generator header and plugging the replacement lead's connector into that connector cavity thereby abandoning the failed lead. However, along with the AIMD, the trifurcated connector considerably increased the mass in a patient's pectoral (or other) pocket. Furthermore, the multitude of leads provided the opportunity for cross connections at the time of initial implant. Also, as the complexity of leads increased so did the chance of lead failure and increased the difficulty and risks associated with subsequent pulse generator or lead replacement/repair surgery.

The ISO 27186 Standard for DF4 and IS4 quadripolar connector systems evolved in order to replace the mechanically and functionally complex trifurcated connector with a single lead connector encompassing multiple sequential electrodes and functions requiring only a single set screw for lead fixation and electrical activation of the pin electrode. This minimized the number and size of connector cavities (ports) in defibrillator headers. In turn, this simplified surgical implant procedures and reduced the risk of technical errors. However, lead conductor failures, particularly of IS4 and DF4 style leads have still occurred.

Failure of an implanted medical lead can occur for a variety of reasons, including dislodgement at or migration from the electrode-tissue interface, complete or partial fracture or breakage of a lead conductor, abrasion or cracking or other forms of lead insulation disruption leading to low insulation resistance and low impedance measurements. Low insulation resistance can occur between a lead conductor and body fluid or between a lead conductor and adjacent lead conductors. Other reasons for failure include an increase in lead conductor impedance, an increase of the pacing capture threshold, or just the failure to deliver appropriate, effective or optimal therapy. As defined herein, a lead conductor failure may include one or more of any of the aforementioned conditions.

When a lead fails it is not always practical to extract an IS4 or DF4 lead even if a single conductor or function has failed. The lead extraction procedure becomes particularly more difficult as the duration of implantation lengthens. Over time, the lead typically becomes adhered to tissue due to the formation of scar tissue, tissue ingrowth and the like thus requiring a more invasive procedure to be performed. On the other hand, simply abandoning a defective IS4 or DF4 lead is problematic, because abandoning the old lead and implanting a new one can lead to venous occlusion and interference with closure of the tricuspid valve leaflets etc. Further, stacked ICD leads with large surface area and high voltage coil electrodes tend to induce significant fibrous tissue reaction, binding the leads together and to the surrounding tissues making extraction procedures even more hazardous. Yet extraction may in some cases become unavoidable because of the development of endocarditis or other complications.

Incorporation of the low and high voltage contacts of an older trifurcated connector defibrillator lead into the newer single DF4 (or its low voltage IS4 counterpart) has a number of functional limitations, but physically DF4 is a great improvement as it: (1) reduces the total volume of the implantable system; (2) reduces the number of set screws required to connect the lead to the defibrillator; (3) reduces the need for tissue dissection within the pocket during replacement; (4) reduces lead-on-lead interactions within the implant site or pocket; and (5) eliminates the potential for DF-1 connectors from being reversed in the defibrillator header. However all of these mechanical and procedural advantages are essentially lost if there is a failure of one of the multiple lead conductors, insulation (and/or their associated electrodes) either through damage or failure to deliver effective therapy.

A failure of one lead conductor in a DF4 system leaves the physician with several bad choices. The physician can put the patient, themselves and their surgical team through a potentially difficult lead explant/extraction surgery and then put in a new DF4 lead. This is not without significant risk. Or, the implanting physician could throw away the still functional defibrillator pulse generator and try to obtain a custom replacement pulse generator with all the original connector cavities including DF4, plus an additional DF-1 connector cavity for a case where a high voltage shocking coil component of the multifunctional lead system has failed, or, plus an additional IS-1 connector cavity where a component of the low voltage pace sense multifunctional lead system has failed. If this type of device was obtainable the physician could then plug the partially defective DF4 lead connector into the new DF4 header connector cavity, implant a new DF-1 lead or IS-1 lead, as indicated and in parallel with the pre-existing DF4 lead system, and insert it into the new header's additional DF-1 or IS-1 connector cavity. However, the new ICD would cost over $20,000 and would need to be specific to not only the DF4 component failure at hand, but also to the specific subtype of ICD being replaced, i.e., single chamber, dual chamber or resynchronization. Further, to date no manufacturer has agreed to produce the series of at least 6 custom ICDs necessary to repair all combinations of lead malfunction and ICD subtypes. The cost of maintaining the whole range of replacement devices in inventory would also be high.

There are a number of problems with abandoned leads, including the problem of MRI RF field-induced overheating of such a lead or its distal electrode. Prior art abandoned lead components are problematic during MRI scans because they can pick up high-power RF induced energy which can lead to overheating of the lead and/or its distal electrode, which can heat up or even burn surrounding heart tissue. Implanted leads are generally less dangerous when they are connected to a pulse generator. The reason for this is that prior art pulse generators, including pacemakers and defibrillators generally have a feedthrough filter capacitor at the point of lead conductor ingress through the hermetic seal of the active implantable medical device. At high frequencies, such as for MRI RF pulsed frequencies, this EMI filter provides a low impedance path between the lead conductors and the AIMD housing which acts as an energy dissipating surface. Accordingly, in a high power MRI environment, much of the RF energy that is induced in the lead is diverted by the feedthrough capacitor where it is dissipated as a small temperature rise on the relatively large surface area of the pacemaker housing, which is usually a titanium housing. However, when a lead is abandoned, there is no place for this MRI RF energy to go other than at the distal tip electrode, which can still be in contact with biological cells. This can lead to significant overheating. For additional information regarding the danger of abandoned lead conductors, one is referred to a published paper entitled, PACEMAKER LEAD TIP HEATING IN ABANDONED AND PACEMAKER-ATTACHED LEADS AT 1.5 TESLA MRI, published in the Journal of Magnetic Resonance Imaging 33:426-431 (2011).

The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted lead wires or devices. For example, for magnetic resonance imaging devices operating at the same magnetic field strength and also at the same SAR level, considerable variations have been found relative to heating of implanted lead wires. It is speculated that SAR level alone is not a good predictor of whether or not an implanted device or its associated lead wire system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5 and 6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and or lead wire systems. It is not likely (other than sudden system shut down) that the static MRI magnetic field can induce currents into the pacemaker lead wire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulse varies with the field strength of the main static field where: RF PULSED FREQUENCY in MHz=(42.56) (STATIC FIELD STRENGTH IN TESLA).

The third type of electromagnetic field is the time-varying magnetic gradient fields designated $B_1$ which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and EMI are induced into an implanted lead wire system. At very low frequency (VLF), voltages are induced at the input to the cardiac pacemaker as currents circulate throughout the patient's body and create voltage drops. Because of the vector displacement between the pacemaker housing and, for example, the TIP electrode, voltage drop across the resistance of body tissues may be sensed due to Ohms Law and the circulating current of the RF signal. At higher frequencies, the implanted lead wire systems actually act as antennas where currents are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the lead wire system (for example, at the header block of a cardiac pacemaker). This has to do with the wavelength of the signals involved and where they couple efficiently into the system.

Magnetic field coupling into an implanted lead wire system is based on loop areas. For example, in a cardiac pacemaker, there is a loop formed by the lead wire as it comes from the cardiac pacemaker housing to its distal TIP, for example, located in the right ventricle. The return path is through body fluid and tissue generally straight from the TIP electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (greater than 450 square centimeters).

An abandoned lead (inactive lead) can heat during an MRI procedure just as an active lead would. However, the abandoned lead is not electrically coupled to an AIMD housing and is therefore not able to dissipate its energy safely into an AIMD housing away from vital body tissue. In some of the prior art, a lead cap has been used to attach to the proximal end of the abandoned lead. The abandoned lead cap can also comprise a significant amount of mass similar to the housing of an AIMD. The abandoned lead cap is then used to help divert energy from the lead itself during an MRI procedure. However, the efficiency and size of the abandoned lead cap is subject to available space limitations inside the human body. Furthermore, a plurality of abandoned lead caps may be required when more than one lead is being abandoned. This can result in too many lead caps being implanted into a patient.

Accordingly, there is a need for a solution that accommodates a variety of abandoned lead configurations without increasing the amount or size of lead caps or AIMDs placed into a particular patient. The present invention fulfills these needs and provides other related advantages.

SUMMARY OF THE INVENTION

An exemplary embodiment a header connector block for an active implantable medical device includes a header block body and at least one active connector cavity configured to be attachable to an active implantable lead. A first conductive leadwire is disposed within the header block body and has a first and second end, where the first end of the first conductive leadwire is electrically connected to the at least one active connector cavity and the second end of the first conductive leadwire is connectable to a conductive feedthrough of a hermetic terminal of the active implantable medical device. At least one abandoned connector cavity is located within the header block body configured to attachable to an abandoned implanted lead. A second conductive leadwire is disposed within the header block body and has a first and second end, where the first end of the second conductive leadwire is electrically connected to the at least one abandoned connector cavity and the second end of the second conductive leadwire is connectable to the active implantable medical device housing.

In other embodiments the at least one active connector cavity may include a plurality of active connector cavities. The at least one active connector cavity may be an ISO IS-1, IS4, DF-1 or DF4 connector cavity. The at least one abandoned connector cavity may be an ISO IS-1, IS4, DF-1 or DF4 connector cavity. The at least one abandoned connector cavity may be an ISO DF-1 connector cavity.

In other embodiments the second conductive leadwire includes a short to the active implantable medical device housing. An RFID tag may be affixed to or embedded within the header block body or the lead adapter.

In other embodiments a lead adapter may be associated with the header, the lead adapter including a header plug configured for to physically insert into and electrically couple to the at least one abandoned connector cavity. The lead adapter may have at least two auxiliary abandoned connector cavities, wherein the at least two auxiliary abandoned connector cavities are electrically coupled to the header plug of the lead adapter, wherein when the lead adapter is connected to the header block body the at least two auxiliary abandoned connector cavities are electrically coupled to the housing through the second conductive leadwire. The at least two auxiliary abandoned connector cavities of the lead adapter may be an ISO IS-1, IS4, DF-1 or DF4 connector cavity. The lead adapter may also have a low profile conforming shape, including an intermediate conformal section between the header plug and the AIMD housing for placing the at least two auxiliary header connector cavities adjacent to an exterior surface of the AIMD when the header plug is placed within the at least one abandoned connector cavity. The lead adapter may be spaced no more than 2 mm from the AIMD exterior surface. The lead adapter has an exterior surface which may tightly conforms to an adjacent AIMD exterior surface.

In another exemplary embodiments of the present invention an active implantable medical device includes an active implantable medical device housing including a hermetic terminal and a header block body attached to the housing. The hermetic terminal includes a plurality of conductive feedthroughs. At least one active connector cavity is located within the header block body configured to attach to an active implantable lead. A first conductive leadwire is disposed within the header block body and has a first and second end, where the first end of the first conductive leadwire is electrically connected to the at least one active connector cavity and the second end of the first conductive leadwire is connected to at least one of the conductive feedthroughs of the hermetic terminal. At least one abandoned connector cavity is located within the header block body configured to attach to an abandoned lead. A second conductive leadwire is disposed within the header block body and has a first and second end, where the first end of the second conductive leadwire is electrically connected to the at least one abandoned connector cavity and the second end of the second conductive leadwire is connected to at least one of the conductive feedthroughs of the hermetic terminal. A diverter circuit has a first and second end, where the diverter circuit is disposed inside the housing, and where the first end of the diverter circuit is electrically coupled to the second end of the second conductive leadwire through at least one of the conductive feedthroughs of the hermetical terminal and the second end of the diverter circuit is connected to the housing.

In other embodiments the diverter circuit may be a short, a resistance, a capacitor, an R-C circuit, an L-C circuit or an R-L-C circuit. The at least one abandoned connector cavity may be an ISO DF-1 connector cavity.

In another exemplary embodiments of the present invention an abandoned implanted lead (auxiliary) header is attachable to an active implantable medical device housing. The abandoned implanted lead header includes a header block body and at least one abandoned connector cavity located within the header block body configured to be attachable to an abandoned implanted lead. A conductive leadwire is disposed within the header block body and has a first and second end, where the first end of the conductive leadwire is electrically connected to the at least one abandoned connector cavity and the second end of the second conductive leadwire is connectable to the active implantable medical device housing.

In other embodiments the second conductive leadwire is connectable to the active implantable medical device housing or a ferrule of the housing by laser welding.

In other embodiments a conductive clip is attached to the header block body, wherein the second end of the second conductive leadwire is electrically coupled to the conductive clip, and where the conductive clip is configured to clip onto the active implantable medical device housing. The at least one abandoned connector cavity may be an ISO IS-1, IS4, DF-1 or DF4 connector cavity.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 2 illustrates a prior art dual chamber bipolar pacemaker with leads implanted into a human heart;

FIG. 2A illustrates an electrical schematic simplification of the structure of FIG. 2;

FIG. 27 illustrates an electrical schematic simplification of the structure of FIG. 3 now with four abandoned lead ports;

FIG. 28A illustrates an electrical schematic simplification of the structure of FIG. 27 wherein there is a single grounded DF-1 port for abandoned leads;

FIG. 28B illustrates a sectional view taken from section 28B-28B from FIG. 28A;

FIG. 28C illustrates another novel lead adapter which was designed to be plugged into the DF-1 cavity of FIG. 28A;

FIG. 28D illustrates a wiring diagram of the lead adapter previously illustrated in FIG. 28C;

FIG. 29 illustrates an electrical schematic simplification of the structure of FIG. 5 now with additional abandoned lead ports;

FIG. 30A illustrates an electrical schematic simplification of the structure of FIG. 29 now with a single abandoned lead port;

FIG. 30B illustrates a sectional view taken from section 30B-30B from FIG. 30A;

DETAILED DESCRIPTION OF THE PREFERRED EMBODIMENTS

Reference is made to section 3 of ISO Standard 27186 as providing definitions to terms and terminology which are used to describe the present invention. Accordingly, as used herein: "bipolar" means having two poles or electrodes; "connector system" refers to an assembly consisting of a lead connector and a connector cavity that are electrically and mechanically joined; "connector cavity" is defined as a cavity within the pulse generator which is intended to receive a lead connector and an identical cavity within a secondary header; "fixation zone" is a zone located in the lead connector pin and within the connector cavity where the lead connector is mechanically secured within the connector cavity; "high-voltage" is defined as electrical potentials greater than 20 volts up to 2000 volts (Note: High-voltages are generally used for defibrillating the heart); "lead connector" or "plug" is the part of the lead that is intended for insertion into the connector cavity of a pulse generator; "lead connector contacts" are defined as conductive elements on the lead connector which include the lead connector pin and lead connector rings; "lead connector pin" is defined as the most proximal conductive element of a lead connector provided for making electrical contact as well as for securing the lead connector within the connector cavity; "lead connector ring" defines angular conductive elements on the lead connector intended for making electrical contact within the connector cavity (Note: the 4-pole or quadpolar connector (DF4 or IS4) has up to 3 lead connector rings and a lead connector pin); "lead electrode" is the distal part of a lead through which electrical impulses are transmitted to or from cardiac tissue (Note: high-voltage electrodes are capable of delivering high-voltage electrical impulses; Low-voltage electrodes are used for transmitting and sensing low-voltage impulses and are generally not suitable for delivering high-voltage); "low-voltage" defines electrical potentials less than or equal to 20 volts; "pulse generator" is any type of active implantable medical device (AIMD) and particularly those devices that deliver electrical energy to effect cardiac rhythms; "securing mechanism" is defined as a mechanism within the connector cavity intended for mechanically securing the lead connector (Note: a securing mechanism can be an active mechanism, such as a set screw or it can be a passive mechanism, such as a spring contact or self-engaging latch; It can also serve a second function of providing electrical contact with the lead connector, as is the case with a set screw); "tripolar" means having three poles or electrodes.

Figure 1:
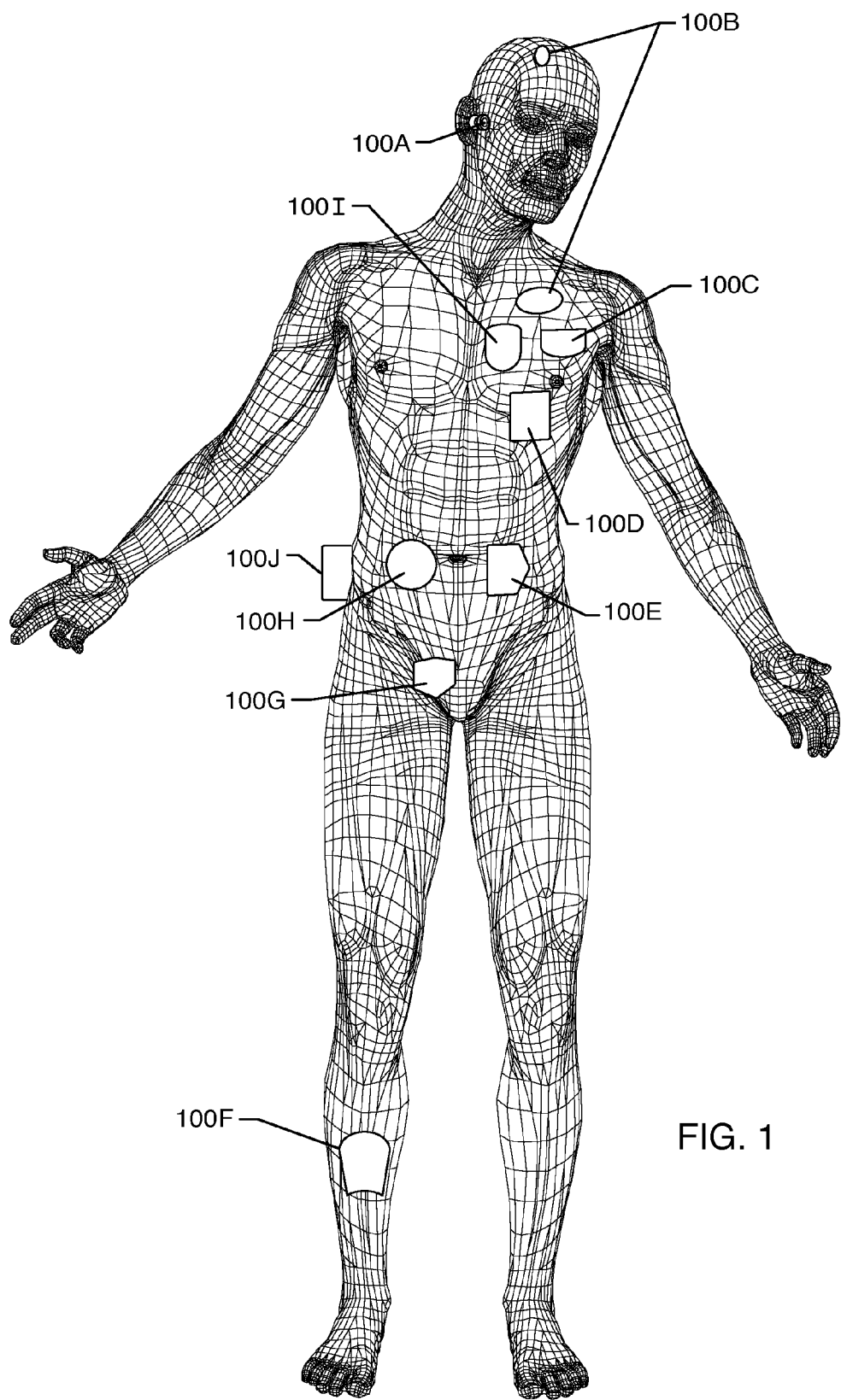
FIG. 1 illustrates a wire form drawing of a human body showing various active implantable medical devices (AIMDs)

FIG. 1 is a wire formed diagram of a generic human body showing a number of exemplary implanted medical devices. 100A is a family of implantable hearing devices which can include the group of cochlear implants, piezoelectric sound bridge transducers and the like. 100B includes an entire variety of neurostimulators and brain stimulators. 100C shows a cardiac pacemaker. 100D includes the family of left ventricular assist devices (LVAD's) and artificial hearts. 100E includes an entire family of drug pumps which can be used for dispensing of insulin, chemotherapy drugs, pain medications and the like. 100F includes a variety of implantable bone growth stimulators for rapid healing of fractures. 100G includes urinary incontinence devices. 100H includes the family of pain relief spinal cord stimulators and anti-tremor stimulators. 100I includes a family of implantable cardioverter defibrillator (ICD) devices, congestive heart failure devices (CHF), and cardio resynchronization therapy devices, otherwise known as CRT devices. 100J illustrates a family of externally worn neurostimulators which are connected to one or more implanted leads (not shown).

Figure 1A:
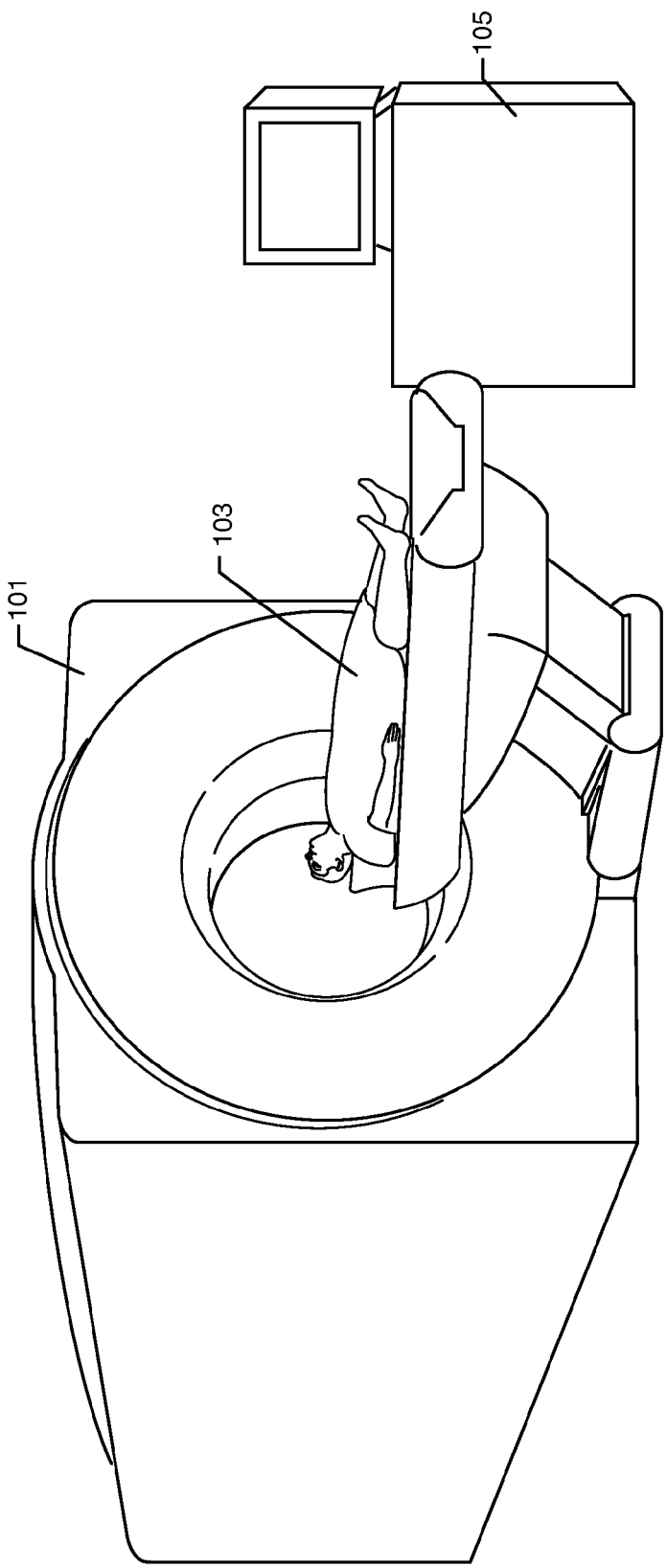
FIG. 1A illustrates a perspective view of a patient who is about to be placed into an MRI scanner.

FIG. 1A illustrates a prior art MRI scanner 101 with a patient 103 about to be positioned within the scanner. Also shown is MRI imaging processing equipment 105.

Figure 1B:
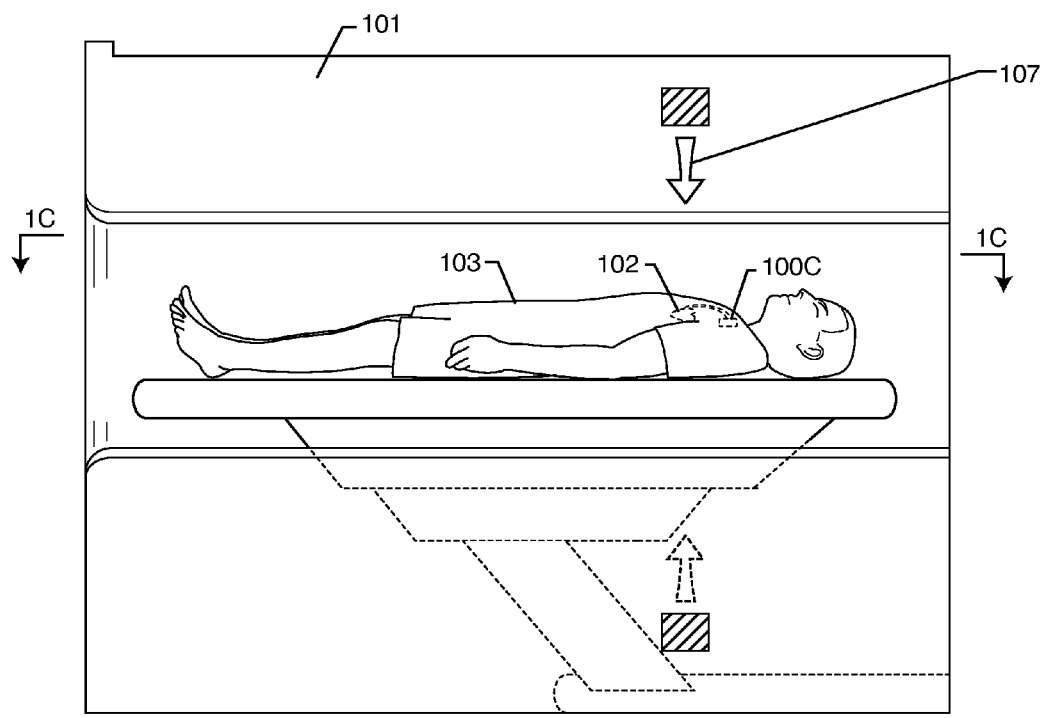
FIG. 1B illustrates a side view of the patient within the scanner showing an intense RF field impinging on the probe or catheter.

FIG. 1B illustrates a side view of the patient 103 placed inside of the scanner 101 and portrays that there is an intense RF field 107 to which the patient's entire body may be exposed. As previously mentioned this intense MRI RF-pulsed field 107 can couple to implanted leadwires of AIMDs such as a cardiac pacemaker 100C and create substantial electromagnetic forces and currents. It is very important that the distal electrodes of implanted leads 104,106 be protected from overheating in such an environment.

Figure 1C:
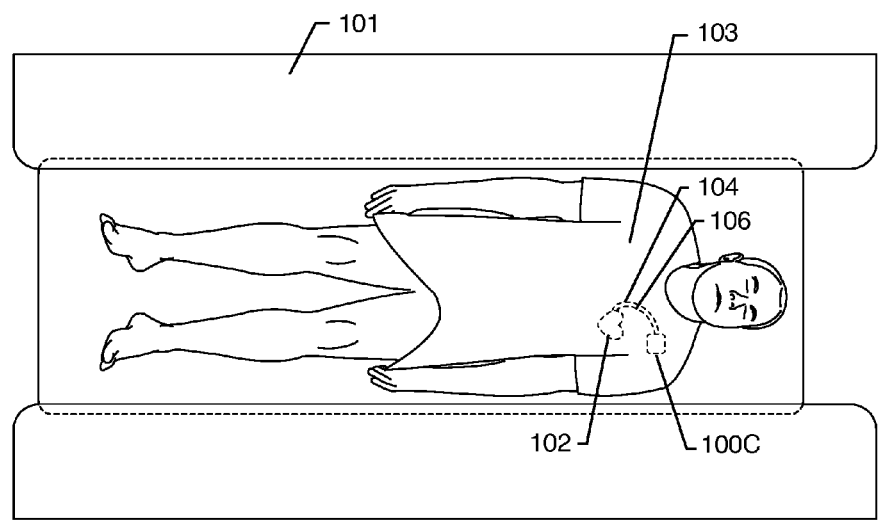
FIG. 1C illustrates a top view of the patient in the MRI scanner.

FIG. 1C is a top view of the patient 103 inside the bore of the MRI scanner 101 with an implanted pacemaker 100C with its associated cardiac leads 104,106.

FIG. 2 shows a prior art outline diagram of the human heart 102 and a cardiac pacemaker 100C. Shown are two implanted bipolar leads 104 and 106 which both have IS-1 connectors 104a, 106a at their proximal ends. Lead 104 is routed transvenously into the right atrium (RA) 108 of the heart 102. Lead 104 is a bipolar lead, meaning that it has two conductors. One of the lead conductors terminates in the distal tip electrode 104b and the other conductor terminates in the distal ring electrode 104c. Implanted lead 106 is routed into the right ventricular cavity (RV) 110. It is also bipolar, meaning that it has two conductors, one of which is connected to the distal tip electrode 106b and the other conductor is connected to the distal ring electrode 106c. This system is known in the art as a dual chamber bipolar pacemaker 100C. The pacemaker 100C has a metallic housing 112 generally of titanium, stainless steel or the like. It also has a non-conductive header block 114 which holds connector assembly components in accordance with ISO Standard IS-1. In this case, the header 114 has two connector cavities 116 and 118 into which the IS-1 lead proximal connectors 104a, 106a can be inserted. Generally, there would be set screws to fix the connector ring and pin electrodes firmly in place (not shown). There are leadwires 120, 120', 122, 122' routed from the connector cavities 116, 118. These four leadwires 120, 120', 122, 122' are routed to a hermetic seal 124 where the wires pass through the housing 112 in non-conductive relation. It is very important that the housing 112 of the AIMD be completely hermetic to protect sensitive electronic components from body fluids, for example, those that are shown on circuit board 126.

FIG. 2A is an electrical schematic simplification of the header 114 and housing 112 shown in FIG. 2. The connector cavities 116 and 118 are shown electrically connected to the leadwires 120, 120', 122, 122' through the hermetic seal 124 to the inside of the housing 112 and electrically coupled to the circuit board 126.

Figures 3, 3A:
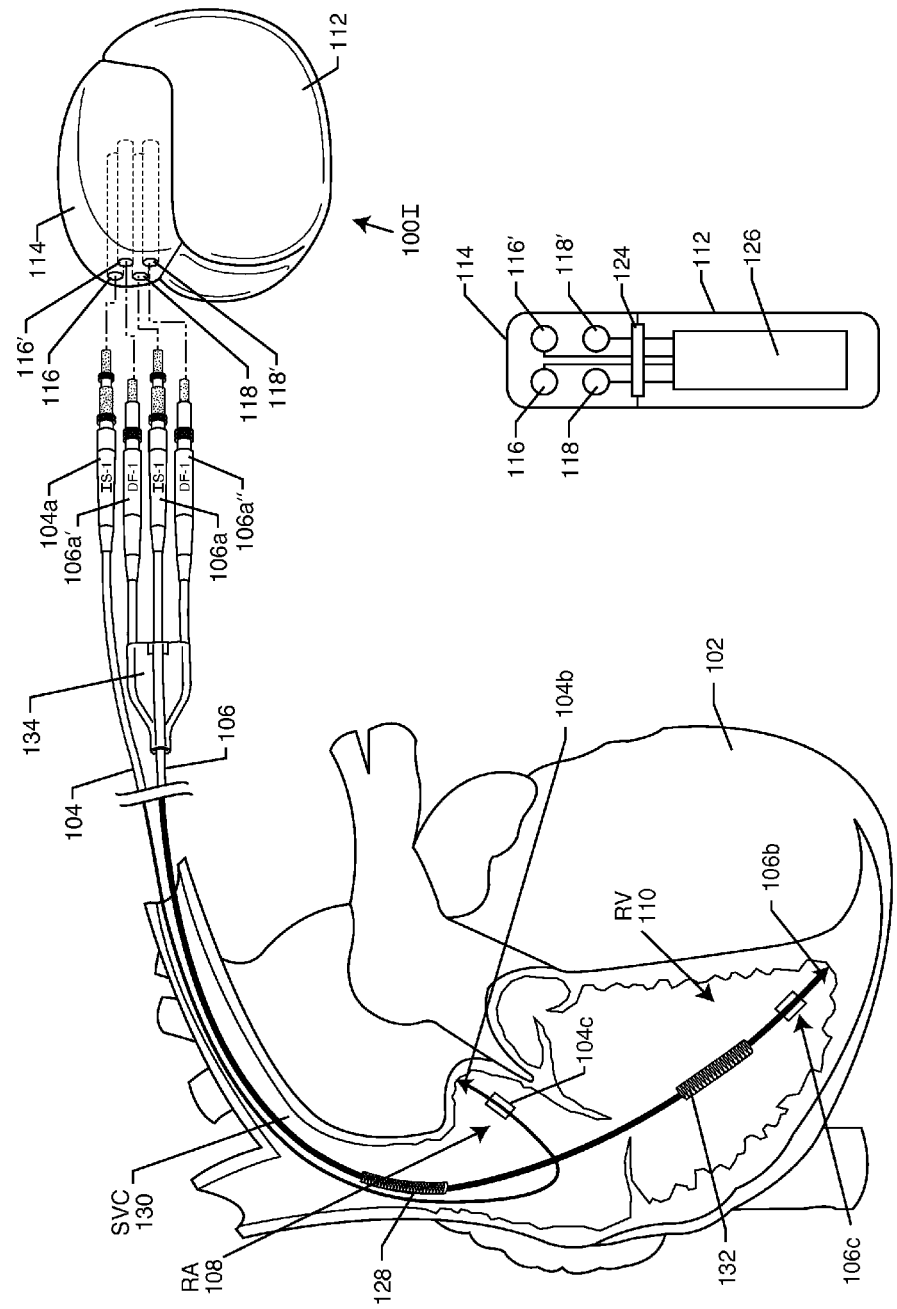
FIG. 3 illustrates a prior art dual chamber implantable cardioverter defibrillator with leads and shocking coils implanted into a human heart.
FIG. 3A illustrates an electrical schematic simplification of the structure of FIG. 3.

FIG. 3 also shows a prior art outline drawing of a human heart 102 and in this case, the device 100I is a dual chamber implantable cardioverter defibrillator. One can see that there are four connector cavities 116, 116', 118, 118' into which the IS-1, DF-1, IS-1 and DF-1 proximal connectors 104a, 106a', 106a, 106a" may be inserted. Again, there are two implanted leads 104 and 106. Bipolar lead 104 is transvenously inserted into the right atrium 108 of the heart 102. It has a distal tip electrode 104b and a distal ring electrode 104c. Quadpolar lead 106 has four conductors. Two of these conductors route to the distal tip electrode 106b and the distal ring electrode 106c. The DF-1 connectors 106a', 106a" are high-voltage conductors. One of the high-voltage connectors 104a' is routed via lead 106 to shocking coil 128, which is generally located in the superior vena cava (SVC) 130 of the heart 102. The second high-voltage shocking coil 132 is located in the right ventricle 110.

In FIG. 3, one can see that there is a trifurcated lead adaptor 134 which combines the connectors 106a', 106a, 106a" for the two high-voltage shocking coils 128, 132 along with one low-voltage tip 106b and ring 106c circuit. In the prior art, excess lead is typically wound up in the pectoral pocket, either adjacent to or around the ICD 100I. The trifurcated adaptor 134 and lead system 104, 106, as shown in FIG. 3, makes for a very bulky pectoral pocket lead arrangement as compared to the arrangement shown in FIG. 2. In addition the four separate connectors and associated proximal lead segments tend to create crisscrossing tissue ingrowth paths. When the ICD 100I needs to be replaced for approaching battery end of life or any other indication, this tangle of insulated conductor segments all tend to have tissue in-growth which makes the surgery difficult as all of these leads must be carefully excised and separated.

FIG. 3A is an electrical schematic simplification of the header 114 and housing 112 shown in FIG. 3. The connector cavities 116, 116', 118, 118' are shown electrically connected by the leadwires through the hermetic seal 124 to the inside of the housing 112 and electrically coupled to the circuit board 126.

Figures 4, 4A:
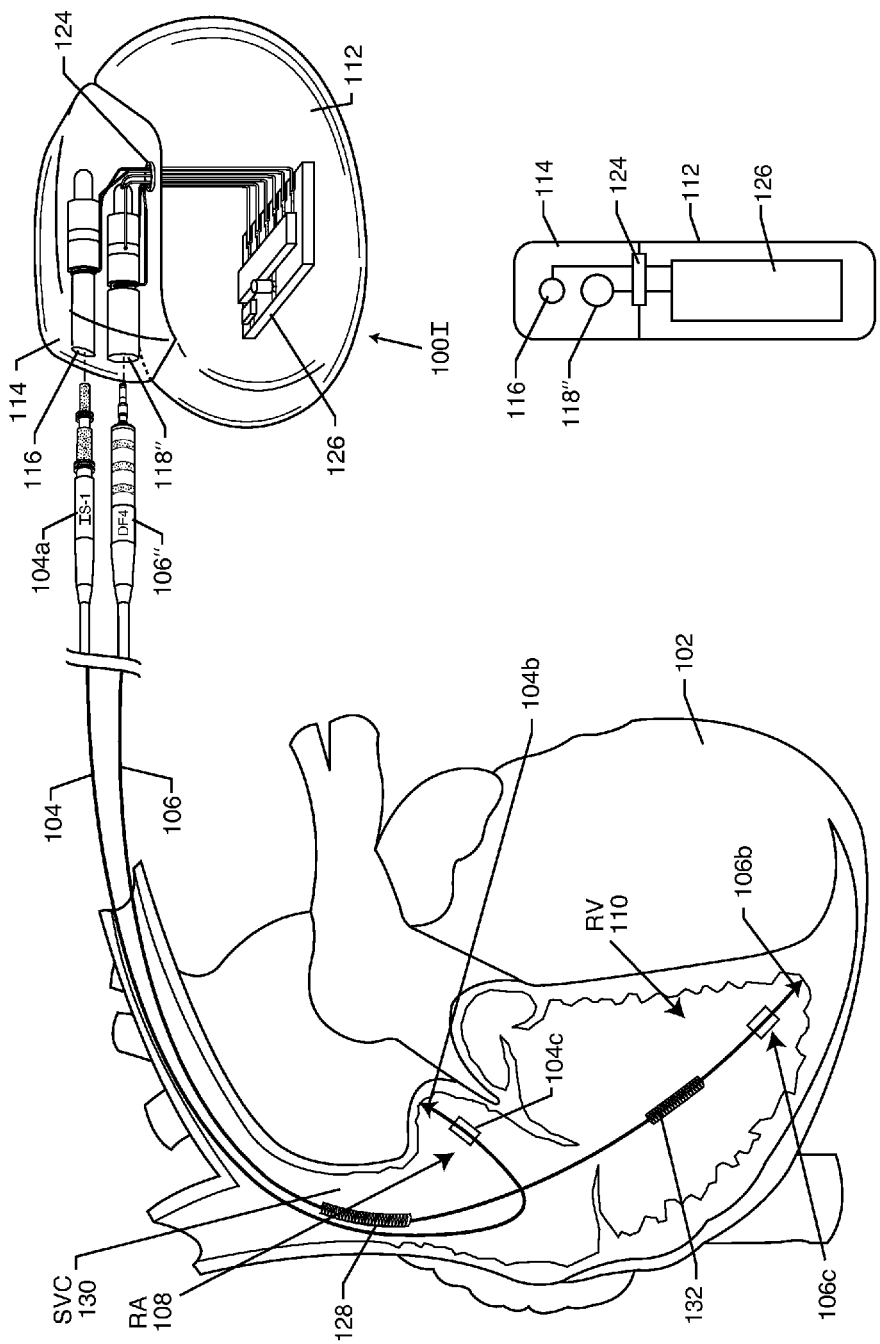
FIG. 4 illustrates a state-of-the-art dual chamber implantable defibrillator similar to FIG. 3 but with the new in-line DF4 quadripolar connector replacing the prior cumbersome trifurcated lead based adaptor.
FIG. 4A illustrates an electrical schematic simplification of the structure of FIG. 4.

FIG. 4 is another prior art cross-section of the human heart 102 again with a dual chamber ICD 100I. As previously illustrated in FIG. 3, the dual chamber ICD 100I has both pacing and high-voltage shocking functions. The electrode placements, both for the high-voltage shocking coils and also the low voltage pace and sense circuits are the same as previously described for FIG. 3. However, in FIG. 4, the defibrillator 100I quadpolar lead 106 incorporates the new state-of-the-art inline quadripolar DF4 proximal lead connector 106" as shown. In this case, there are now only two connector cavities 116 and 118" in the defibrillator 100I header 114. Connector cavity 116 is a low-voltage connector cavity for receipt of the bipolar IS-1 proximal connector 104a. Connector cavity 118" is a DF4 quadripolar connector cavity designed to receive the DF4 proximal connector 106". In this case, there are still two leads 104 and 106 that are routed down into the various chambers of the heart as previously described in FIG. 3. When one considers that excess lead is wound up in the ICD pocket, one can see that the configuration in FIG. 4 is vastly superior to the trifurcated connector 134 as previously illustrated in FIG. 3. The surgical implant procedure is considerably simplified and there is a lot less bulk created in the pacemaker pocket which increases both reliability and patient comfort.

FIG. 4A is an electrical schematic simplification of the header 114 and housing 112 shown in FIG. 4. The connector cavities 116 and 118" are shown electrically connected by the leadwires through the hermetic seal 124 to the inside of the housing 112 and electrically coupled to the circuit board 126.

Figures 5, 5A:
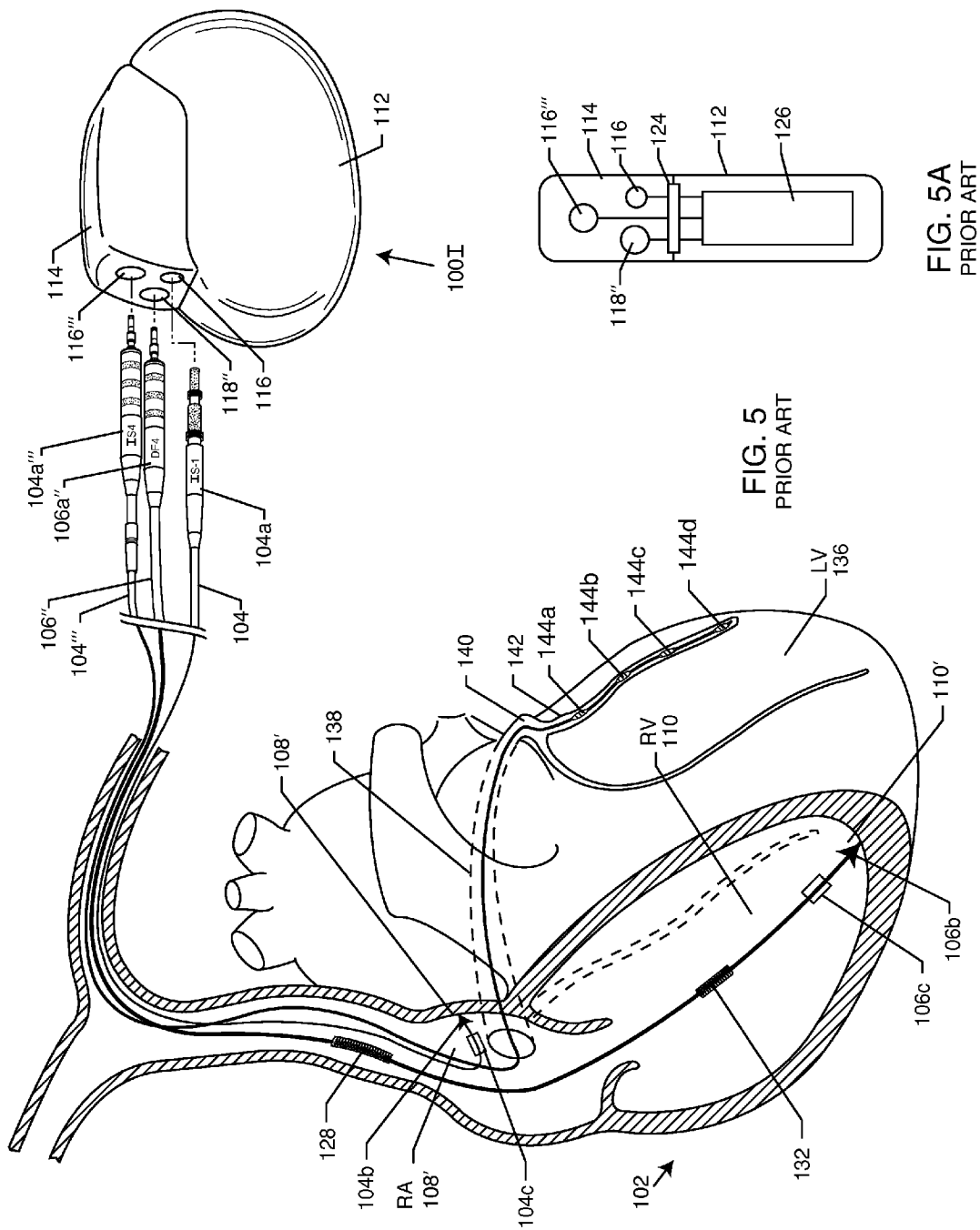
FIG. 5 illustrates a prior art dual chambered ICD that also employs a quadripolar left ventricular lead for simultaneous stimulation of the right and left ventricles, so called cardiac resynchronization therapy or CRT, with both DF4 and IS4 quadripolar leads.
FIG. 5A illustrates an electrical schematic simplification of the structure of FIG. 5.

FIG. 5 is a prior art drawing of a human heart 102 and ICD 100I that is state-of-the-art. This defibrillator system not only has high-voltage shocking and low-voltage pacing functions, but it also has cardiac resynchronization therapy (CRT) capabilities through electrodes placed transvenously into the right atrium 108 and then through the coronary sinus 138 into epicardial veins 140, 142 on the surface of the left ventricle (LV) 136. In this case, there are two types of quadripolar connectors being used at the proximal lead ends. There are three implanted leads 104, 104''' and 106". Lead 104 is a low-voltage bipolar lead which is routed to distal tip 104b and ring 104c electrodes in the right atrial appendage 108'. Lead 106" is a quadripolar low-voltage/high-voltage lead. Lead 106" contains four conductors, two of which are connected to high-voltage shocking coils 128 and 132. There are also two low-voltage conductors in lead 106" which are routed to the distal tip electrode 106b and distal ring electrode 106c in the right ventricular apex 110'. The third lead 104''' is a low voltage four-conductor IS4 or quadripolar lead which is routed transvenously through the coronary sinus 138, the great cardiac vein 140 and into a branch vessel 142 which is part of the epicardial or surface venous system draining blood from the left ventricle 136 back into the right atrium 108. Shown are four electrodes 144a through 144d. The IS4 proximal connector for lead 104''' is plugged into connector cavity 116''' on the header block 114 of the ICD 100I. The DF4 connector 106a" is plugged into connector cavity 118" and the IS-1 proximal connector 104a is plugged into connector cavity 116 as shown.

FIG. 5A is an electrical schematic simplification of the header 114 and housing 112 shown in FIG. 5. The connector cavities 116''', 116 and 118" are shown electrically connected by the leadwires through the hermetic seal 124 to the inside of the housing 112 and electrically coupled to the circuit board 126.

Figure 6:
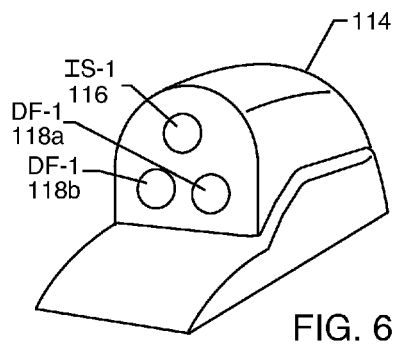
FIG. 6 illustrates the header block of a prior art implantable single chamber defibrillator showing two high-voltage DF-1 connector cavities and a single low-voltage IS-1 connector cavity.

FIG. 6 illustrates a prior art header connector block 114 of a prior art AIMD with two high-voltage connector cavities 118a, 118b which are both DF-1 and a low-voltage bipolar connector cavity 116 in accordance with IS-1. Each high-voltage connector cavity 118a, 118b would be unipolar and routed to a defibrillation shock coil 128, 132 (not shown). The low-voltage connector cavity 116 would be bipolar and routed to a distal tip 104b and ring 104c electrode (not shown).

Figure 7:
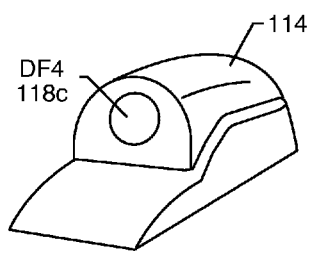
FIG. 7 illustrates how the new quadripolar DF4 connector provides equivalent function to FIG. 6 but with one rather than three primary header connector cavities.

FIG. 7 is exactly the same system illustrated in FIG. 6 except that the three connector cavities have been replaced with a single DF4 quadripolar connector or cavity 118c. In this case, both the high-voltage and the low-voltage functions are all in one DF4 connector.

Figure 8:
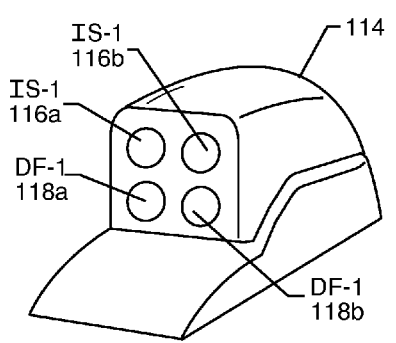
FIG. 8 illustrates a dual chamber defibrillator header with both atrial and ventricle connector cavities where the high-voltage connector cavities are DF-1 and the right ventricular and atrial connector cavities are IS-1.

FIG. 8 is the header 114 of a dual chamber defibrillator with DF-1 high-voltage connector cavities 118a, 118b. In addition, there are two low-voltage connector cavities 116a and 116b. One for a lead to be routed to the right ventricle 110 and the other to the right atrium 108. In this case, there would be two DF-1 connectors and two IS-1 connectors at the proximal ends of the required leads.

Figure 9:
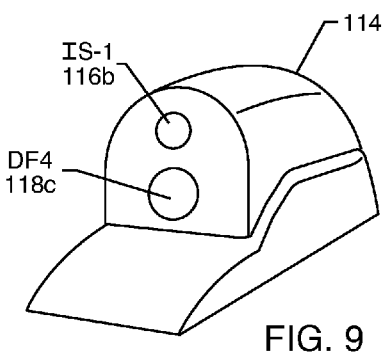
FIG. 9 is the state-of-the-art equivalent to FIG. 8 wherein both DF-1 connector cavities and one IS-1 connector cavity have been replaced by a single inline DF4 quadripolar connector.

FIG. 9 shows how the inline quadripolar DF4 connector 146 can be used to reduce four connector cavities 118a, 118b, 116a and 116b to two cavities 118c and 116b. This is a logical progression from what is described in FIGS. 6 and 7. One connector cavity 118c would be DF4 for streamlined provision of both low voltage ventricular pacing and sensing, and in addition dual coil high voltage defibrillator function. The second connector cavity 116b, would be IS-1 bipolar capable of providing atrial electrical stimulation and sensing.

Figure 10:
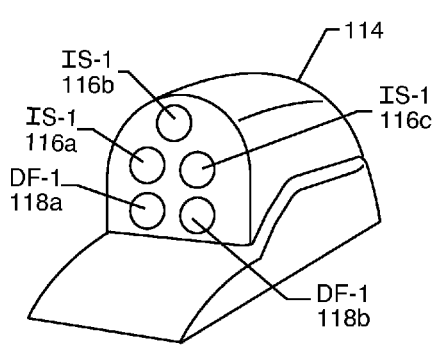
FIG. 10 illustrates a dual chamber defibrillator with CRT capability.

FIG. 10 shows a dual chamber defibrillator primary header 114 with the addition of CRT functions requiring a total of five connector cavities. The two high-voltage connector cavities 118a, 118b are DF-1 and the low voltage connector cavities 116a, 116b and 116c are IS-1 connectors. Required leads and intended functions are identical to what is described in detail above. The additional, fifth low-voltage connector cavity is for receipt of an IS-1 type connector, whereby, a fifth lead would be routed through the venous system into the right atrium 108, the coronary sinus 138 and from there into sub-epicardial branch coronary veins near the lateral surface of the left ventricle, (see FIG. 5).

Figure 11:
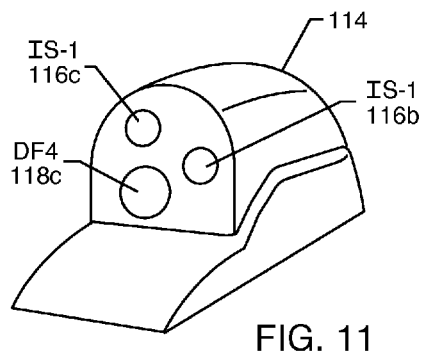
FIG. 11 is the modern equivalent of FIG. 10 showing a DF4 quadripolar connector that replaces the two high voltage DF-1 connector cavities and the one IS-1 connector cavity.

FIG. 11 shows the system of 10 simplified from five to three connector cavities. The DF4 cavity 118c provides for combined dual coil high-voltage functions and the low voltage bipolar pace sense function, all into the newly standardized quadripolar connector. There is still a necessity to have a low-voltage connector cavity 116c for an IS-1 lead to be routed to the left ventricle and also an atrial connector cavity 116b for a second IS-1 lead to be routed to the right atrium.

Figure 12:
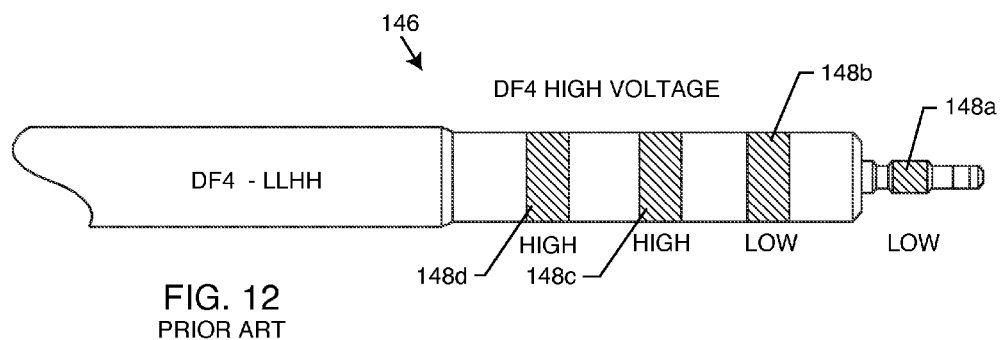
FIG. 12 illustrates an enlarged pictorial view of an embodiment of a proximal end portion of a DF4 high-voltage connector.

FIG. 12 is an enlarged pictorial view of an embodiment of a proximal end portion of a DF4 high-voltage connector 146. As can be seen, at its proximal tip, it has a low-voltage pin electrode connection contact 148a and it also has a low-voltage contact ring 148b next in line. In addition, it has two high-voltage contact rings 148c and 148d. This makes for a four-conductor lead as previously described as lead 106a" in FIG. 5. This is the same as the DF4 lead 106" previously shown in FIG. 4.

Figure 13:
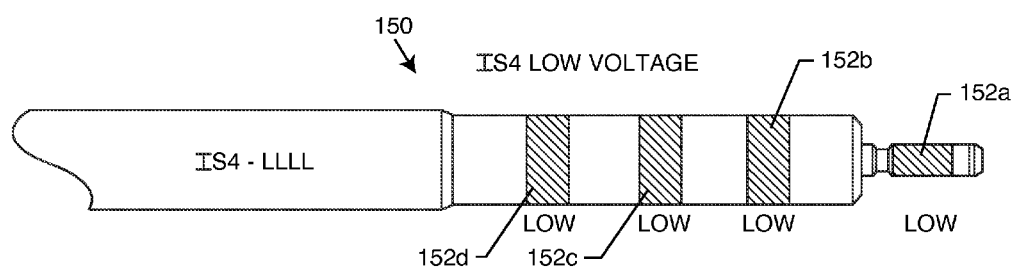
FIG. 13 illustrates an enlarged pictorial view of an embodiment of a proximal end portion of an IS4 low-voltage quadripolar lead connector.

FIG. 13 is an enlarged pictorial view of an embodiment of a proximal end portion of an IS4 low-voltage quadripolar lead connector 150. As illustrated, the connector 150 comprises a low-voltage connector tip 152a and three low-voltage contact rings 152b, 152c and 152d. This is the same as the low-voltage IS4 left ventricular lead 104a''' as previously described in FIG. 5.

Figure 14:
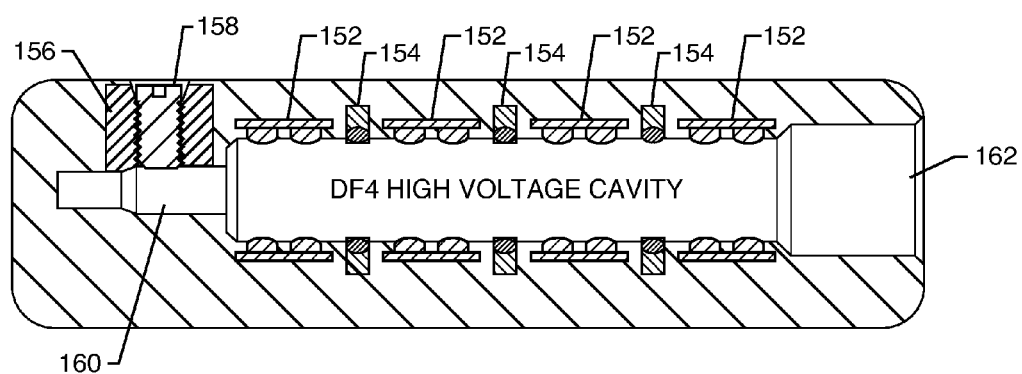
FIG. 14 illustrates an ISO DF4 high voltage cavity.

FIG. 14 illustrates an ISO DF4 high voltage cavity. This is otherwise known as a port in a header block for an AIMD. It has an opening for port 162 to receive the proximal end connector of an implanted lead (not shown). There are multiple seals 152 to prevent ingress of body fluids and moisture. There are electrical contact rings 154 as shown. These contact rings are designed to mate up with corresponding ring contacts of the proximal connector (not shown). There is also a tip area 160 to receive the tip of the connector. Set screw 158 would be firmly seated against the low voltage pin electrode connection contact 148a (not shown). There are leadwires (not shown) attached to connector block 156 and to each of the electrical contact rings 154.

Figure 15:
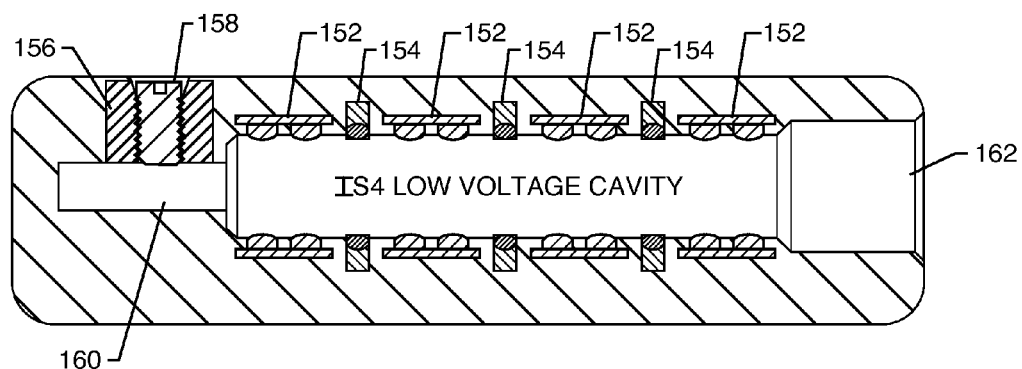
FIG. 15 illustrates an IS4 low voltage cavity which is very similar to FIG. 15.

FIG. 15 is an IS4 low voltage cavity which is very similar to FIG. 15.

Figure 16:
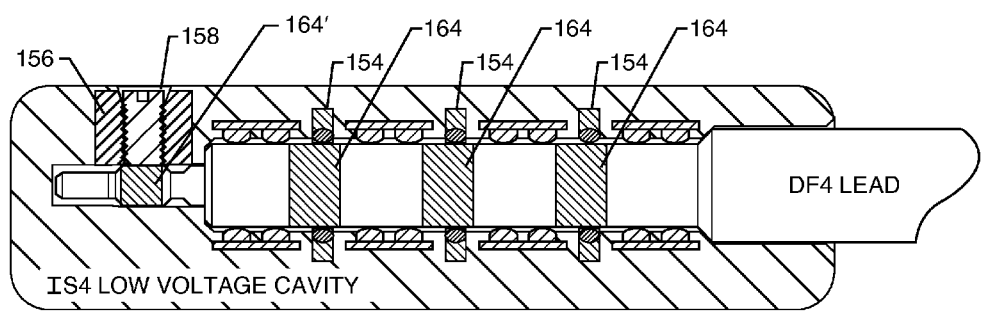
FIG. 16 illustrates an IS4 low voltage cavity with a DF4 proximal connector improperly inserted into it.

FIG. 16 illustrates an IS4 low voltage cavity with a DF4 proximal connector improperly inserted into it; however, it will still work. In the DF4 Standard, a DF4 lead, when inserted into a low voltage cavity, will make proper electrical contact in all four of its points.

Figure 17:
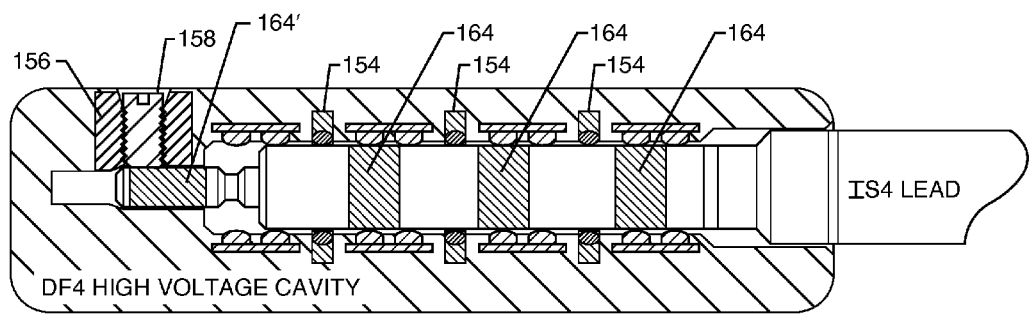
FIG. 17 illustrates a DF4 high voltage cavity with an IS4 lead inadvertently plugged into it.

FIG. 17 illustrates the opposite situation. In this case, we have a DF4 high voltage cavity with an IS4 lead inadvertently plugged into it. This is a highly dangerous situation in that the active implantable medical device, such as an ICD, could inadvertently provide a high voltage pulse to low voltage circuits. This is why the IS4 lead is locked out and will not properly fit into the DF4 high voltage cavity. Referring once again to FIG. 16, one will see that the contact rings 164 all line up and make contact with the corresponding connector ring 154, which are connected to leadwires (not shown). Also, the set screw 158 lines up and makes direct contact with contact ring 164'. Referring once again to FIG. 17, one will see in the locked-out situation, the low voltage IS4 contact rings 164 will not properly line up with the corresponding contacts 154. This provides a safe guard open circuit so that high voltage cannot inadvertently be applied to low voltage electrodes implanted in the heart.

Figure 18:
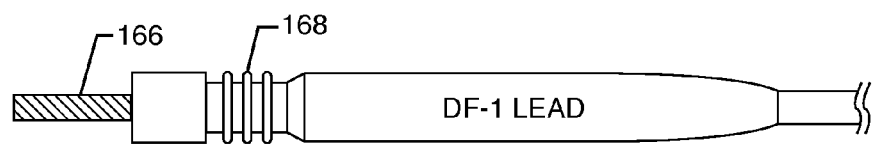
FIG. 18 illustrates a pictorial view of a DF-1 high voltage proximal lead connector.

FIG. 18 is a pictorial view of a DF-1 high voltage proximal lead connector. One will see that it is unipolar and has a tip connector 166.

Figure 19:
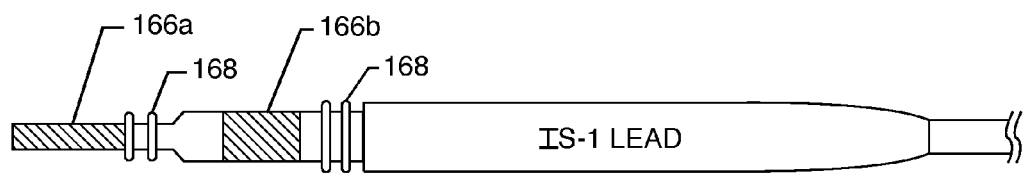
FIG. 19 illustrates an IS-1 bipolar low voltage proximal lead connector.

In contrast, FIG. 19 illustrates an IS-1 bipolar low voltage proximal lead connector, which has a distal tip connector 166a and a ring connector 166b. Referring once again to FIGS. 18 and 19, one can see that there are multiple molded seals 168 to preclude ingress of body fluids or moisture.

Figure 20:
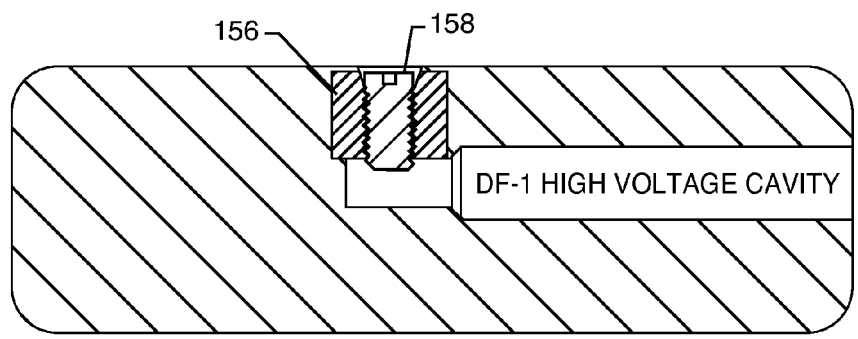
FIG. 20 illustrates a sectional view of a DF-1 high voltage connector cavity that is ready to receive the proximal connector previously illustrated in FIG. 18.

FIG. 20 is a sectional view of a DF-1 high voltage connector cavity that is ready to receive the proximal connector previously illustrated in FIG. 18. It is unipolar and is designed to be held in place by set screw 158.

Figure 21:
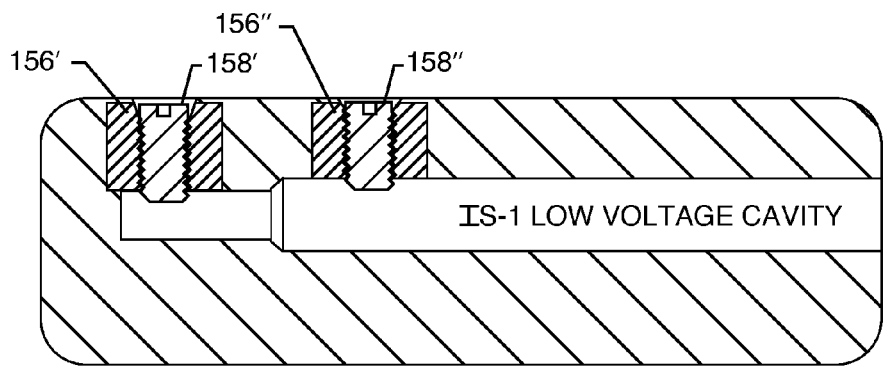
FIG. 21 illustrates an IS-1 low voltage connector cavity which is ready to receive the proximal IS-1 connector previously illustrated in FIG. 19.

FIG. 21 is very similar to FIG. 20 and illustrates an IS-1 low voltage connector cavity which is ready to receive the proximal IS-1 connector previously illustrated in FIG. 19. In this case, there are two set screws 158' and 158" which both firmly affix the lead connector in place and also make electrical contact to contact points 166a and 166b.

Figure 22:
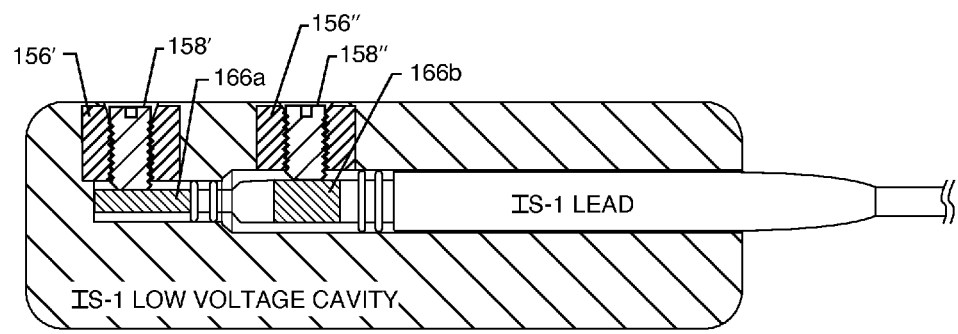
FIG. 22 illustrates the IS-1 proximal lead connector previously shown in FIG. 19 and inserted into the IS-1 low voltage connector cavity previously illustrated in FIG. 21.

FIG. 22 illustrates the IS-1 proximal lead connector previously shown in FIG. 19 and inserted into the IS-1 low voltage connector cavity previously illustrated in FIG. 21. One can see that set screws 158' and 158" make both an electrical and a mechanical connection to contacts 166a and 166b.

Figure 23:
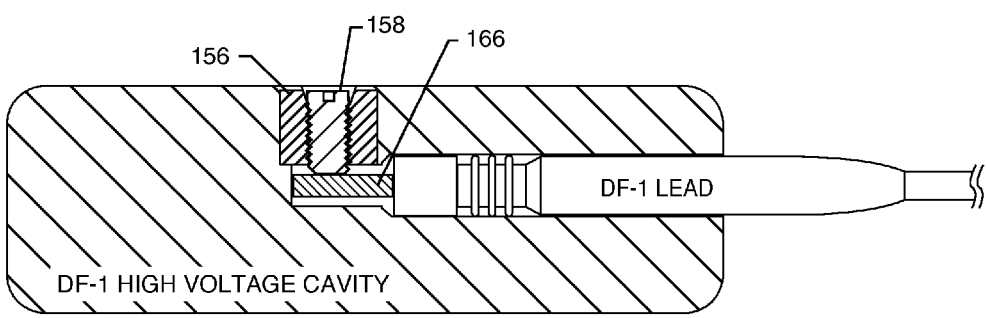
FIG. 23 illustrates the DF-1 proximal connector previously illustrated in FIG. 18 inserted into the DF-1 high voltage connector cavity previously illustrated in FIG. 20.

FIG. 23 is very similar to FIG. 22 and shows the DF-1 proximal connector previously illustrated in FIG. 18 inserted into the DF-1 high voltage connector cavity previously illustrated in FIG. 20. Again, set screw 158 makes mechanical and electrical connection to the contact area 166.

Figure 24:
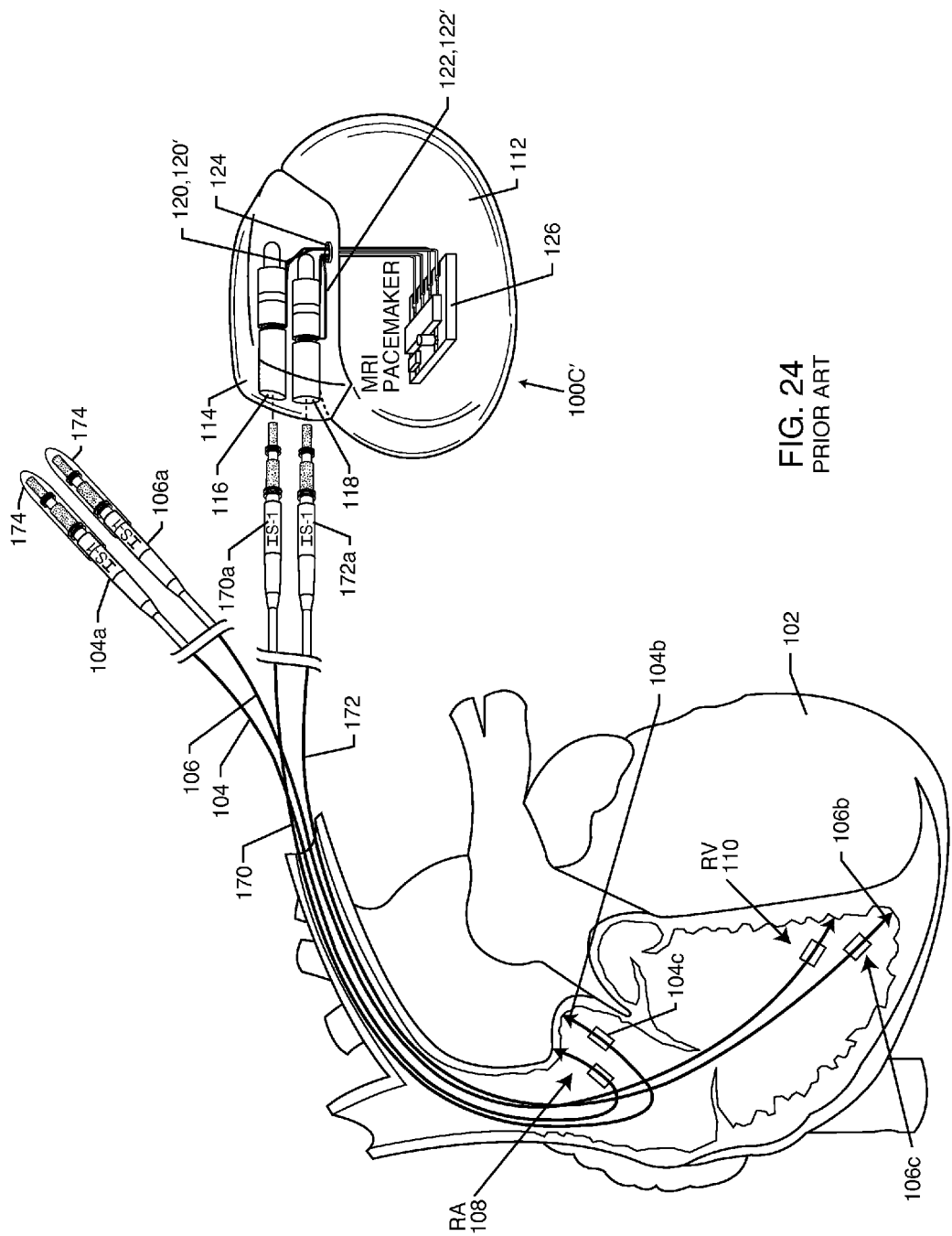
FIG. 24 is similar to the prior art dual chamber bipolar system previously illustrated in FIG. 2 and now illustrates a pre-existing pacemaker 100C which has been removed.

FIG. 24 is very similar to the prior art dual chamber bipolar system previously illustrated in FIG. 2. In this particular case, the patient had a pre-existing pacemaker 100C which has been removed. For various reasons, it is desirable to implant an MRI approved pacemaker and corresponding lead system. ISO Joint Working Group 2 and regulatory agencies have determined that in order to receive MRI approval for implantation, both the leads and the device must be matched as a system. It is absolutely contraindicated to mix an MRI approved pacemaker with a different set of leads that were not MRI approved at the same time. In other words, the AIMD and its leads operate together as a system. These MRI approved systems have been carefully designed such that the leads will not dangerously overheat during MRI scans, the AIMDs will not exhibit abnormal circuit behavior caused by electromagnetic interference, the device will not reset, the gradient fields will not introduce intrinsic or erroneous pulses on the lead and the like. The physics of MRI and the dangers implicit in MRI scanning of an implanted AIMD are more thoroughly described in U.S. Pat. No. 7,945,322, the contents of which are herein incorporated by reference. Referring once again to FIG. 24, an MRI conditionally approved pacemaker is being implanted along with its matched MRI conditionally approved leads 170 and 172. The preexisting leads 104 and 106 are shown abandoned off to the side of the pacemaker pocket. However, it is well known that abandoned leads present special dangers during MRI scanning. One is referred to a paper entitled, PACEMAKER LEAD TIP HEATING IN ABANDONED AND PACEMAKER-ATTACHED LEADS OF 1.5 TESLA MRI, that was published in the Journal of Magnetic Resonance Imaging 33:426-431 (2011) by Langman, et al. FIG. 2 of the Langman paper illustrates that the distal electrode of an abandoned lead can heat up as much as 30 degrees centigrade in temperature rise. This type of temperature rise could be very dangerous and damaging to cardiac tissue. Referring once again to FIG. 24, one can see that the abandoned leads 104 and 106 are still connected to cardiac tissue at their distal electrodes. One approach would be to simply extract these leads. However, lead extraction is a very costly and invasive procedure. There are also many possible complications associated with lead extraction, including excess bleeding, perforation and even death. One can see in FIG. 24 that it is common practice in the prior art to place the silicone end cap 174 over the proximal connectors of abandoned leads. This is in order to prevent body fluid ingress and bacterial ingress down into the lead body itself. The interior spaces of lead bodies are excellent places for bacteria to hide and even prosper in the face of antibiotics. Accordingly, the silicone leak caps 174 are generally very important for this purpose. However, placement of the silicone lead caps also means there is no place for MRI induced RF energy to escape from the lead other than in its distal tip electrodes which is in contact with myocardial tissue. Referring back to FIG. 2 of the Langman paper, one will see that when the cap is removed from the abandoned leads, they actually heat up less.

Figure 25:
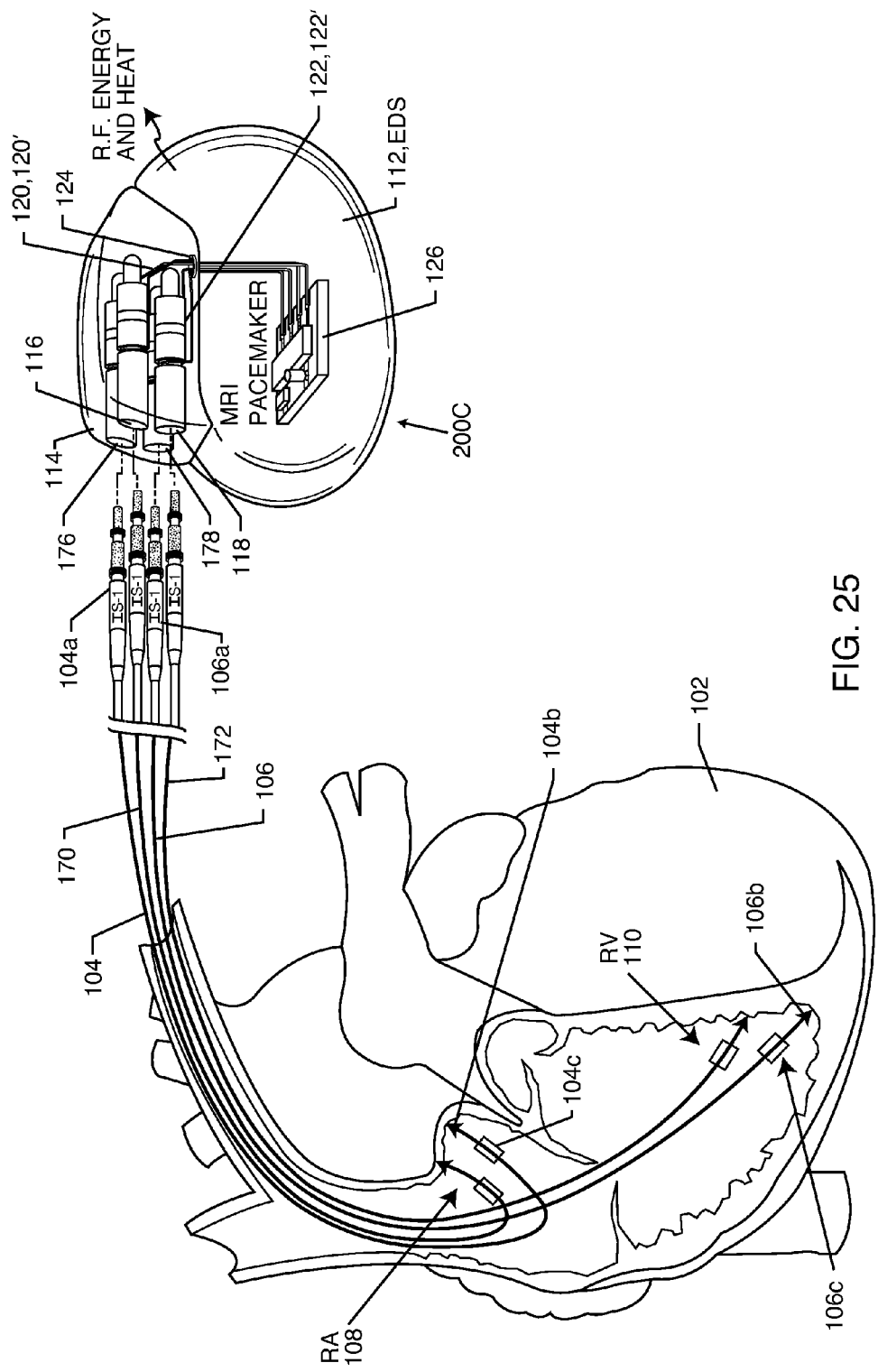
FIG. 25 is exactly the same system as in FIG. 24 now illustrating the MRI approved pacemaker with two extra ports.

FIG. 25 is exactly the same system as previously illustrated in FIG. 24 except that in this case, the MRI approved pacemaker has two extra ports 176 and 178. The two added ports 176 and 178 have their connector contacts routed through the header block where they are directly connected to the pacemaker housing 112. In other words, these two new ports short out the abandoned lead connectors to the device housing, which acts as an RF energy and heat dissipating surface 112. Testing by the inventors, which would be further described in FIG. 41, prove that connection of abandoned leads to an energy dissipating surface at the proximal end, will effectively cool the distal end. One is also referred to U.S. Pat. Nos. 8,000,801 and 8,200,342, the subject of which is abandoned lead caps which are herein incorporated by reference.

Figure 25A:
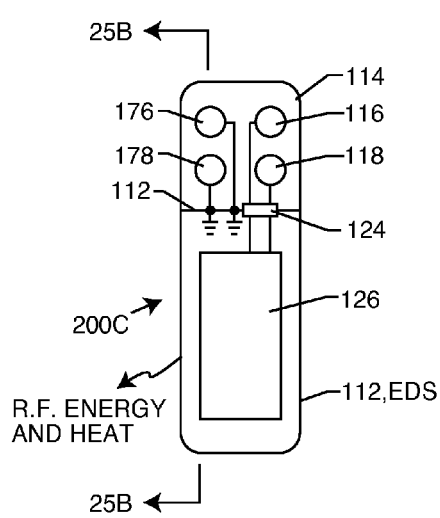
FIG. 25A illustrates an electrical schematic simplification of the structure of FIG. 25.

FIG. 25A is an end view showing the four connector ports. As one can see, connector ports 176 and 178 have their leadwires grounded right to the AIMD housing 112. Active ports 116 and 118 provide for normal pacing and sensing as previously described in FIG. 2.

Figure 25B:
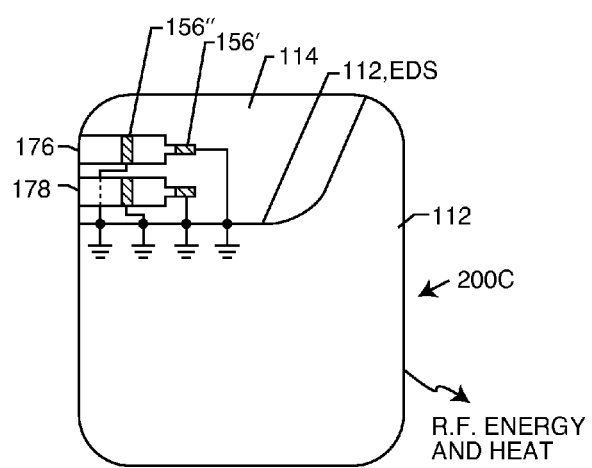
FIG. 25B illustrates a sectional view taken from section 25B-25B from FIG. 25A.

FIG. 25B is a sectional view taken from section 25B-25B from FIG. 25A. One can see the side view of the two IS-1 connector ports 176 and 178. Each one of the contact rings and tips has been grounded directly to the conductive AIMD housing 112 through the connector blocks 156' and 156". In this case, the AIMD housing 112 acts as an RF energy and heat dissipation surface which literally draws MRI RF-induced energy out of the implanted (abandoned) leads and dissipates it over the relatively large surface area of the pacemaker itself. By dissipating energy over a large surface area, one can dissipate said energy without unduly overheating the surrounding surfaces. In contrast, when one dissipates a great amount of RF energy at, for example, a distal tip electrode, a very significant temperature rise occurs because it's being dissipated over such a tiny surface area in small contact from the electrode to the surrounding body tissues. Also, in general, dissipating the energy in the pocket of an AIMD is far preferable to having said energy dissipated in a sensitive organ or a nerve. For example, in a pacemaker application, dissipation of RF energy or heat in myocardial tissue can damage sensitive myocardial tissue itself. In marked contrast, the pectoral pocket is either subcutaneous (just below the skin surface) or below the pectoral muscle. Neither the skin, the fat, nor the muscle in these areas is particularly sensitive to thermal injury as compared to myocardial tissue. Similar analogies can be made for deep brain stimulators and deep brain tissue, spinal cord stimulators and the like. It is highly undesirable to overheat brain tissue or spinal cord tissues in contrast to providing a few degrees of temperature rise in muscle or fat.

Referring once again to FIG. 25, one can see that a negative to providing these two extra connector ports is an increase in size of the header block 114. In other words, having a two port pacemaker is more volumetrically efficient as compared to having a four port pacemaker. The present invention will address adapters as a means of minimizing the number of additional connector ports.

Figures 26A, 26B:
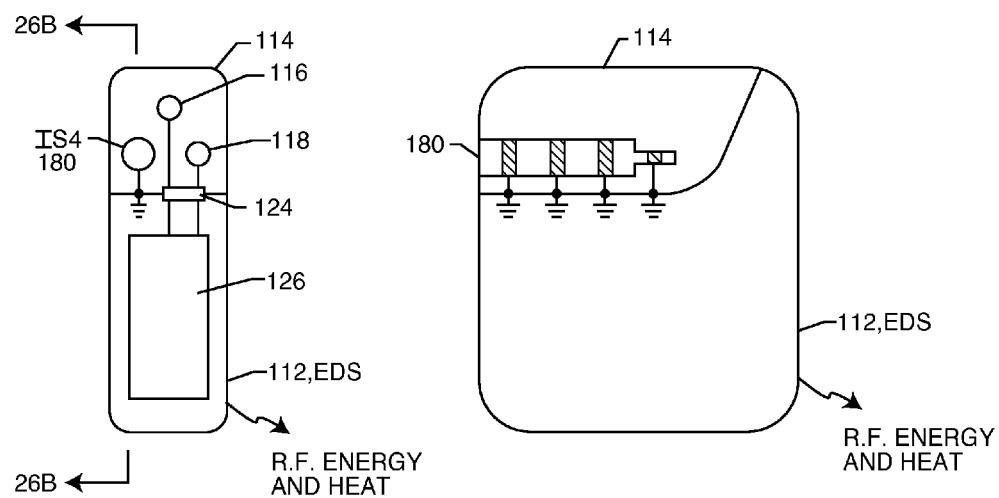
FIG. 26A illustrates an electrical schematic simplification of the structure of FIGS. 25 and 25A using a single grounded IS4 port instead of two grounded IS-1 ports.
FIG. 26B illustrates a sectional view taken from section 26B-26B from FIG. 26A.

FIG. 26A is the end view of an MRI approved pacemaker which uses a single grounded IS4 port instead of two grounded IS-1 ports 176 and 178 as previously described in FIG. 25. In this case, there are still two active IS-1 ports 116 and 118 that perform all of the same functions as previously illustrated in FIG. 2. These active ports are routed through a hermetic insulator 124 and in turn, leadwires are connected to circuit board 126.

FIG. 26B is taken from section 26B-26B from FIG. 26A and illustrates that all three of the contact rings and the contact tip of the IS4 connector are directly grounded to the AIMD housing 112 which acts as an RF heat and energy dissipating surface. Using a grounded IS4 connector port is particularly preferred for several reasons. First of all, it was previously demonstrated that a DF4 proximal connector plug will mate properly with a low voltage IS4 connector. As shown in FIGS. 26A and 26B, the preferred IS4 port is labeled as 180. In the present invention, other types of ports could also be grounded. For example, the present invention is inclusive of all types of AIMD leads and connector systems, including those used in neurostimulators, cochlear implants, spinal cord implants and the like as previously described in FIG. 1. In other words, by using cardiac pacemakers and implantable defibrillators as an example, one will understand the concepts of the present invention.

Figure 26C:
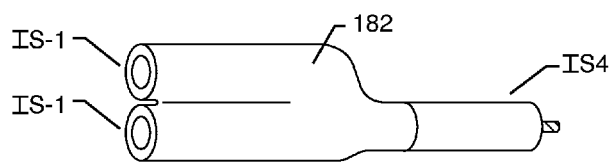
FIG. 26C illustrates a novel lead adapter of the present invention.

FIG. 26C illustrates a novel lead adapter 182 of the present invention. It has a proximal IS4 connector which is designed to plug into the grounded connector port 180 as previously described in FIGS. 26A and 26B. This adapter provides two female IS-1 connector cavities into which the abandoned leads 104 and 106 may be readily inserted.

Figure 26D:
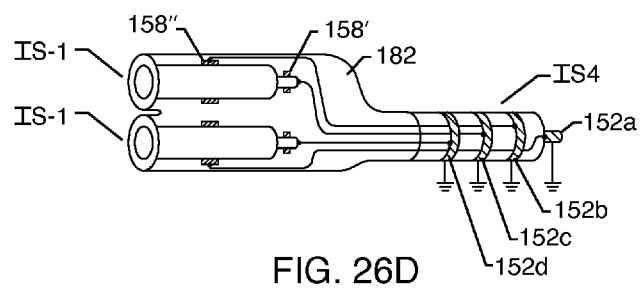
FIG. 26D illustrates a partial sectional view showing the internal leadwires of the adapter of FIG. 26C.
Figure 26E:
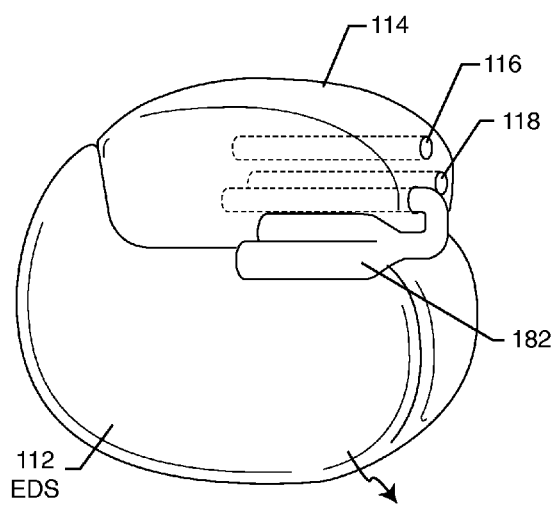
FIG. 26E illustrates a novel lead adapter conforming to the shape of the AIMD housing.
Figure 26F:
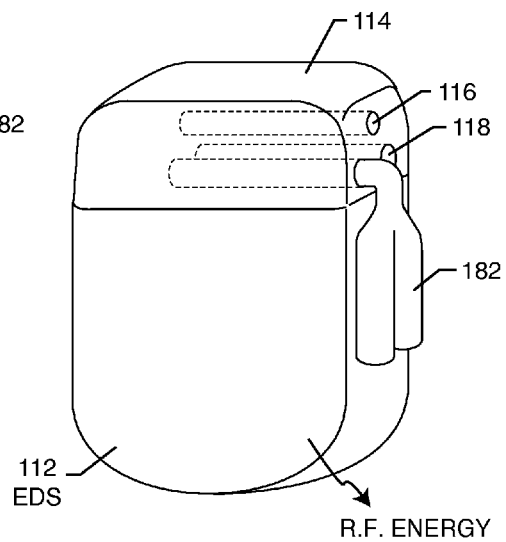
FIG. 26F illustrates another novel lead adapter conforming to the shape of the AIMD housing.

FIG. 26D is a partial sectional view showing the internal leadwires of the adapter of FIG. 26C. One can see that both of the IS-1 ports, both of their bipolar contacts have been routed to the three ring connectors and tip connector of the IS4 proximal connector plug. When the IS4 plug of FIG. 26C or 26D is inserted into the connector cavity 180 of FIGS. 26A and 26B, one will see that this has the effect of grounding all of the conductors of the two abandoned leads 104 and 106. Referring once again to FIG. 26D, one can see that there are contact rings 158" and tip contact 158' in the connector cavities. Leadwires are routed from these points to the four IS4 proximal plug contact rings 152b, 152c and 152d. There is also a wire run to the contact tip 152a. Again, when these are inserted into the main connector cavity as illustrated in FIG. 26B, each of these points is grounded. Referring once again to FIG. 26C, an inline lead adapter like this is not particularly efficient because it is stiff and it tends to increase the overall length of the pacemaker and increases the amount of surgery and the size of the corresponding pocket. In a more preferred embodiment, the lead adapter may be bent as illustrated in FIG. 26E and shaped so that it conforms very closely to the shape of the pacemaker housing 112. This type of low profile lead adapter accordingly, is a preferred embodiment. An alternative preferred embodiment is shown in FIG. 26F wherein the lead adapter 182 is bent down, again, to closely conform to the pacemaker shape.

FIG. 27 is the end view of an MRI approved implantable cardioverter defibrillator, as previously illustrated in FIG. 3. Shown are four abandoned lead ports 176, 176', 178 and 178'. These are similar to the grounded ports previously illustrated in FIGS. 25A and 25B. The active ports 116, 116', 118 and 118' are routed to a hermetic seal 124 where the leadwires are connected to circuit board 126. In terms of volumetric efficiency, FIG. 27, which is reading on the implant system of FIG. 3, is a more extreme example. What is meant by this, referring to FIG. 3, is that we had a device with four ports and in FIG. 27, we now have an MRI approved device with eight ports. Eight ports are unacceptably large in terms of volumetric efficiency. Referring once again to FIG. 27, one can see that the old and now abandoned leads have been plugged into grounded ports 176, 176', 178 and 178'. The new MRI conditionally approved leads are now routed to the ports of the MRI conditionally approved AIMD as a system. Accordingly, the new leads are inserted into ports 116, 116', 118 and 118', where leadwires are routed through hermetic seal 124 and connections are made to internal circuit board 126.

An improved embodiment is illustrated in FIG. 28A, wherein there is a single grounded DF-1 port 180. The active ports 116, 116', 118 and 118' have been rearranged in the header port to be more volumetrically efficient and lower in profile. One can see that the header port 114 of FIG. 28 is substantially shorter than the header port previously illustrated in FIG. 27. This volumetric efficiency is very important, especially for patient comfort.

FIG. 28B is a sectional view taken from section 28B-28B from FIG. 28A illustrating the DF-1 connector cavity 180. One can see that it is unipolar and there is a single ground at point 156 to the AIMD housing 112. If there is only a single ground wire, in this case, the ground wire must be highly conductive and great enough in cross-section area to be able to dissipate the RF energy from a multiplicity of implanted leads.

FIG. 28C illustrates a lead adapter 182, which was designed to be plugged into the DF-1 cavity 180 previously illustrated in FIGS. 28A and 28B. Referring once again to FIG. 28C, one can see that this particular lead adapter provides three IS-1 ports and one DF-1 port for grounding of all of the abandoned leads previously illustrated in FIG. 3.

FIG. 28D is a wiring diagram of the lead adapter previously illustrated in FIG. 28C. One can see that each of the rings 158" and tips 158' have been connected together and then routed through a single ground wire 184 to the DF-1 tip electrode 166. This tip contact 166 becomes grounded when the adapter is plugged into the connector cavity 180 as previously illustrated in FIG. 28B. Leadwire 184 also needs to be highly conductive and sufficiently large in cross-sectional area to be able to dissipate enough RF energy from all four of the abandoned leads. Referring once again to FIG. 28D, it will be appreciated that the single leadwire 184 could be replaced by a multiplicity of leadwires that all terminate at point 166. The lead adapter in FIG. 28C is shown as a straight or inline adapter in a similar fashion to that previously illustrated in FIG. 26C. One will appreciate that the inline adapter, as shown in FIG. 28C, could be reshaped into a closely fitting adapter, more like those shown in FIG. 26E or FIG. 26F.

FIG. 29 shows the end view of a header block of an MRI approved pacemaker with added ports for the abandoned leads. Port 176 is an IS4 port to receive the abandoned IS4 lead 104''' previously described in FIG. 5. Port 176' is a grounded port designed to receive the abandoned DF4 lead 106'' previously described in FIG. 5. Port 178 is a grounded IS-1 port designed to receive the abandoned lead 104 previously described in FIG. 5. There are three new active ports in the MRI approved pacemaker to receive three MRI leads. These new leads would be newly implanted at the time of implantation of the new AIMD, as shown in FIG. 29. Port 116''' is an active IS4 port, active port 118'' is a new DF4 port and active port 116 is a new IS-1 port. Again, referring to FIG. 29, one can see that additional header height is necessary to accommodate these six ports.

FIG. 30A is taken from FIG. 29 except that the three shorted or abandoned ports 176, 176' and 178 have been combined into a single unipolar DF-1 port 180.

FIG. 30B is taken from section 30B-30B from FIG. 30A and illustrates that the DF-1 connector cavity 180 has been grounded at point 156 to the AIMD housing 112 which acts at an energy dissipating surface.

Figure 30C:
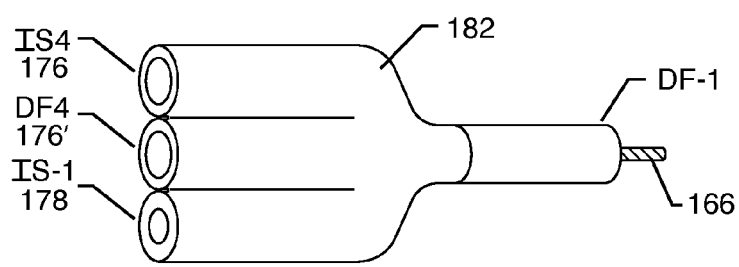
FIG. 30C illustrates a novel lead adapter with a DF-1 proximal port and tip which is designed to be inserted into the connector cavity as previously illustrated in FIG. 30B.

FIG. 30C is an illustration of a lead adapter with a DF-1 proximal port and tip 166 which is designed to be inserted into the connector cavity 180 as previously illustrated in FIG. 30B. This adapter provides ports for abandoned leads 176 (IS4), 176' (DF4) and 178 (IS-1).

Figure 30D:
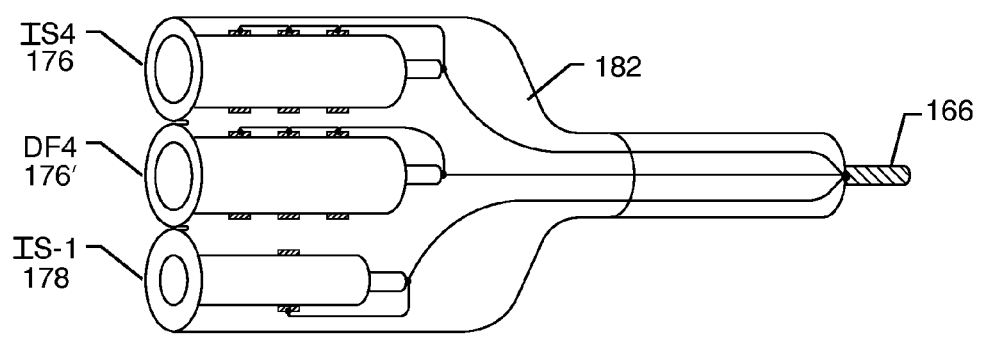
FIG. 30D illustrates the wiring diagram of the structure of FIG. 30C.

FIG. 30D is the wiring diagram associated with FIG. 30C. As one can see, each of the ports 176, 176' and 178 has its own leadwiring which connects all of its contact rings and tips to the proximal contact tip 166. This use of three leadwires routed to contact tip 166 divides up the RF current and therefore minimizes inductance and voltage drop and maximizes the amount of RF energy that will be diverted to the AIMD housing 112.

Figure 31:
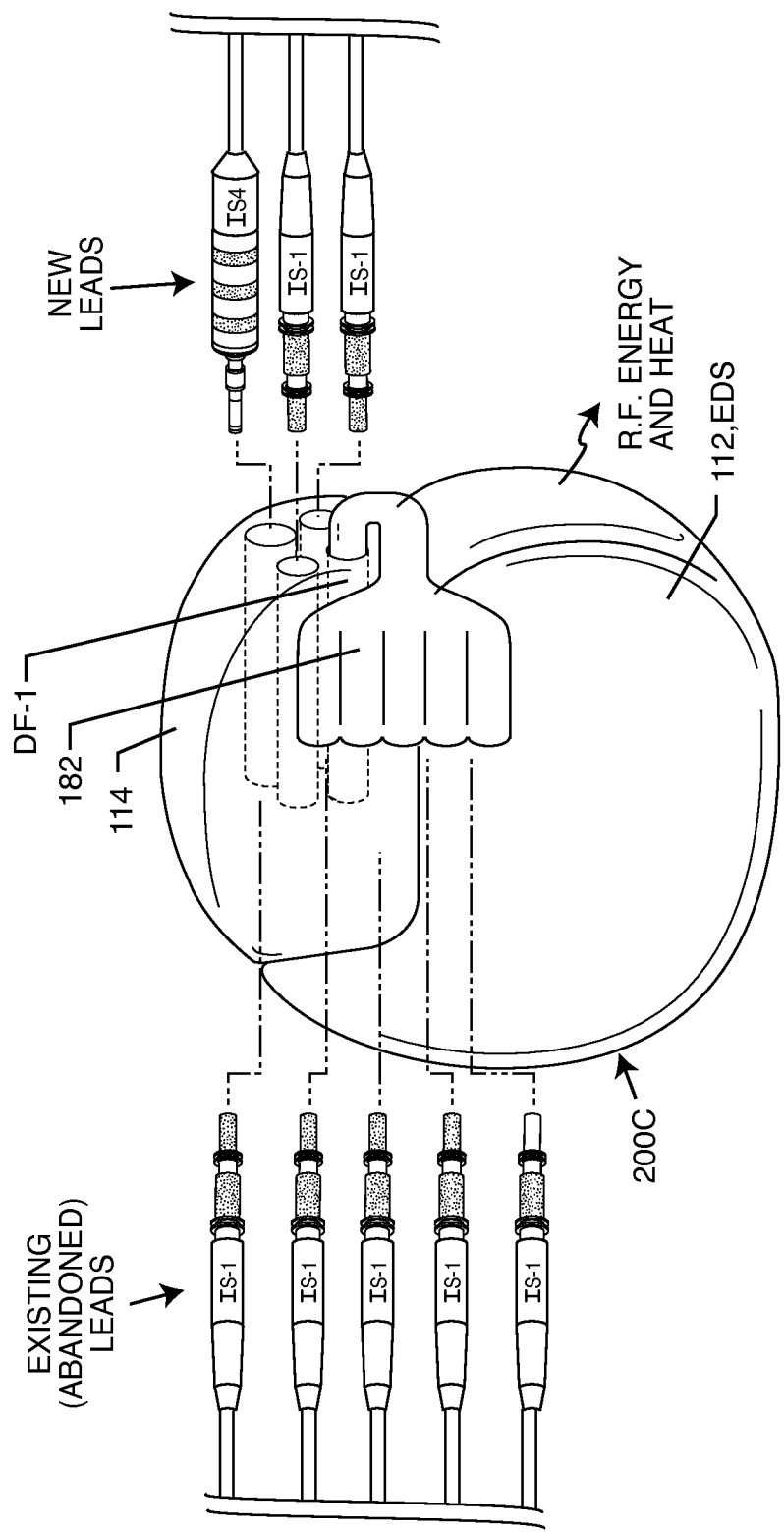
FIG. 31 illustrates a general AIMD with an adapter which adapts from a DF-1 connector cavity, which is grounded, to five ports.

FIG. 31 illustrates a general AIMD with an adapter 182 which adapts from a DF-1 connector cavity, which is grounded, to five ports. This adapter 182 can be five ports, six or any number as required for a particular application. Shown are five abandoned IS-1 leads and then new active leads IS4, IS-1 and IS-1. It has been approximated that patients with abandoned leads make up about 20% of the installed patient population for cardiac rhythm management devices. Currently, these patients are completely contraindicative to receive an MRI scan even if they receive an MRI approved pacemaker and lead system. In fact, the inventors are aware of cases where the patient has a serious neurological deficit and is in desperate need of an MRI scan. In this case, the entire pre-existing system must be explanted along with explantation of all of the leads. Then a new MRI approved pacemaker and new leads are installed. It is impractical to provide a specialized MRI approved pacemaker with ports for every possible type of abandoned lead. The amount of inventory that would be required and the cost associated with such inventory, is simply not possible. Accordingly, it is a preferred embodiment in the present invention that a single grounded DF-1 or IS4 grounded port be provided along with a variety of relatively inexpensive lead adapters. These lead adapters can be inventoried by the hospital in sterile packs and can be ready to use with any number or type of lead system.

Figure 32A:
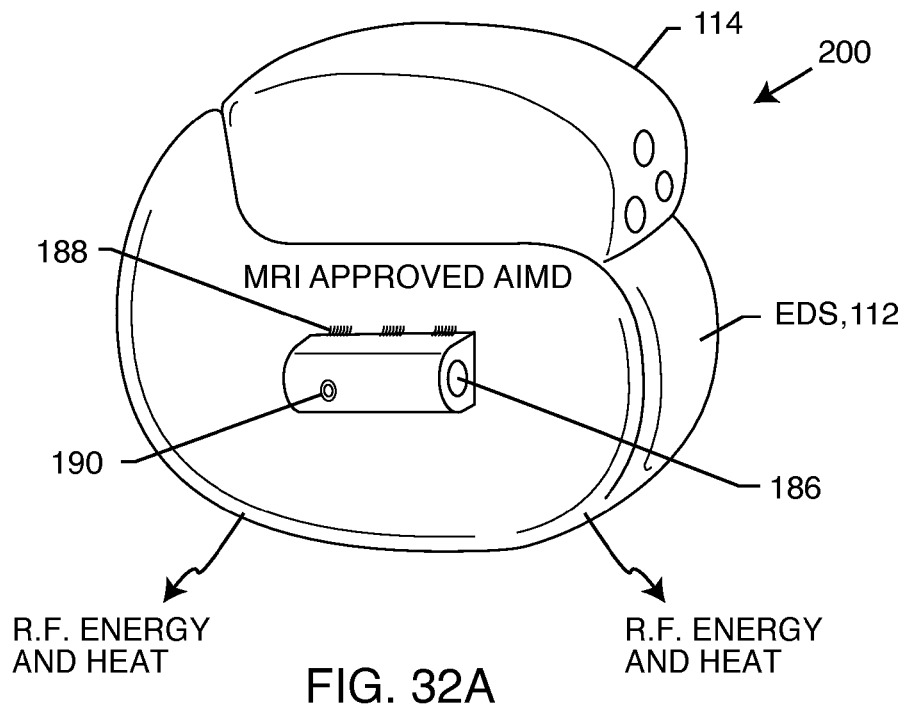
FIG. 32A illustrates a perspective view of an AIMD now with a grounded DF-1 connector port attached in a location on the side of the AIMD housing.

FIG. 32A is a pictorial view of an AIMD 200 which has a header block 114. In this case, a grounded DF-1 connector port 186 has been attached in a location on the side of the AIMD housing in order to receive any of the DF-1 adapters of the present invention. This port 186 provides a way to attach any number of abandoned leads. There is a set screw 190 to make electrical and mechanical connection to the DF-1 proximal contact tip. Any of the adapters as previously illustrated, for example, in FIG. 30C, could be used in conjunction with the novel AIMD of FIG. 32A. In this way, the AIMD header 114 can be relatively small in size and each one can be designed in the same fashion. Referring once again to FIG. 32A, one can see that there are multiple ground contact points 188 in order to evenly distribute RF energy over a wide surface area of the AIMD housing 112.

Figure 32B:
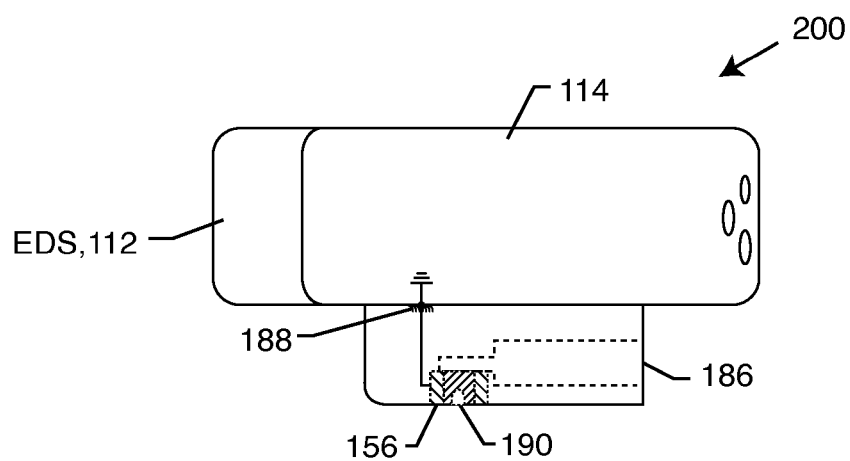
FIG. 32B is a top view taken from FIG. 32A showing the interior details of the DF-1 connector cavity.

FIG. 32B is a top view taken from FIG. 32A showing the interior details of the DF-1 connector cavity 186.

Figure 32C:
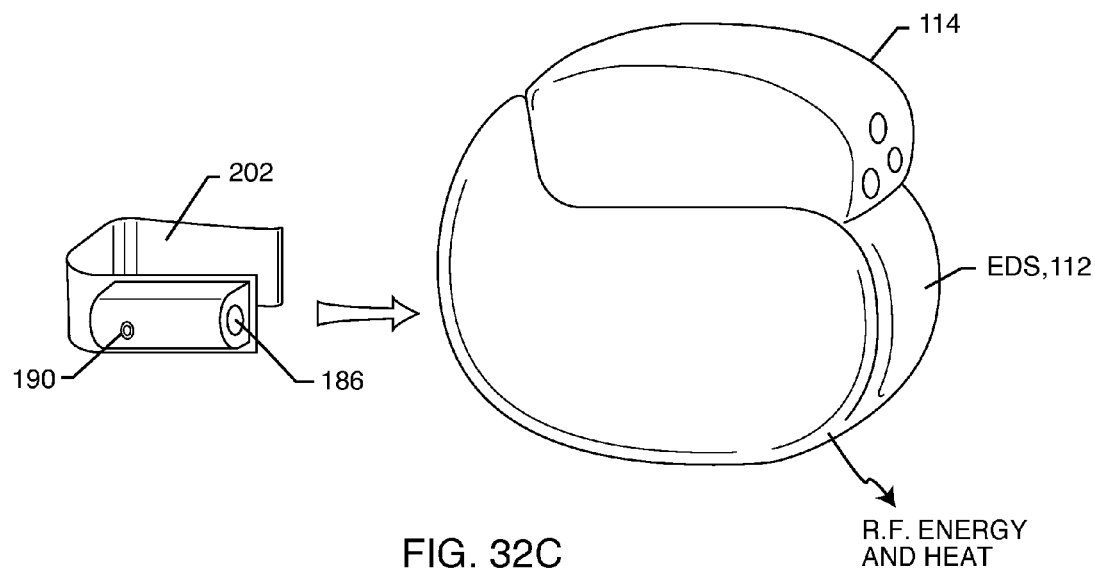
FIG. 32C illustrates a clip to which the DF-1 grounded connector port has been attached and solidly grounded.

FIG. 32C illustrates a clip 202 to which the DF-1 grounded connector port 186 has been attached and solidly grounded. Set screw 190 is used to affix a DF-1 proximal male adapter (not shown). The clip 202 is designed to tightly slip onto the housing 112 of an AIMD. This allows any AIMD to be rapidly and readily adapted for grounding of abandoned leads, including the previously described adapters.

Figure 32D:
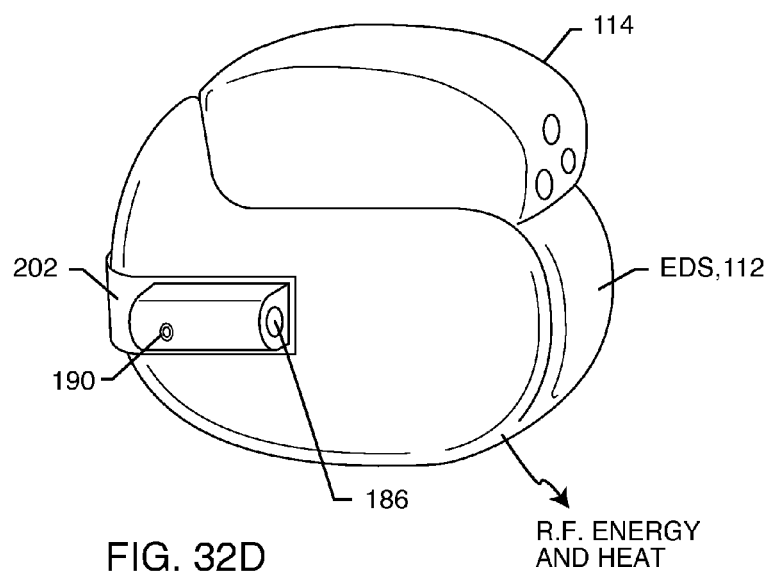
FIG. 32D illustrates the grounding clip of FIG. 32C mated with the AIMD.

FIG. 32D shows the grounding clip 202 of FIG. 32C mated with the AIMD. Spring tension keeps the adapter 202 and its associated connector port 186 held firmly in place. It is important that a significant amount of tension occur in clip 202 such that the connection between the grounding clip 202 and the AIMD housing is highly conductive so that maximal MRI RF energy is shunted from the implanted lead conductor to the EDS housing 112. It is also important that the material of the grounding clip 202 be of suitable biocompatible and non-toxic metal. Titanium, gold-plated titanium or stainless steel is a preferred material for the clip 202.

Figure 33:
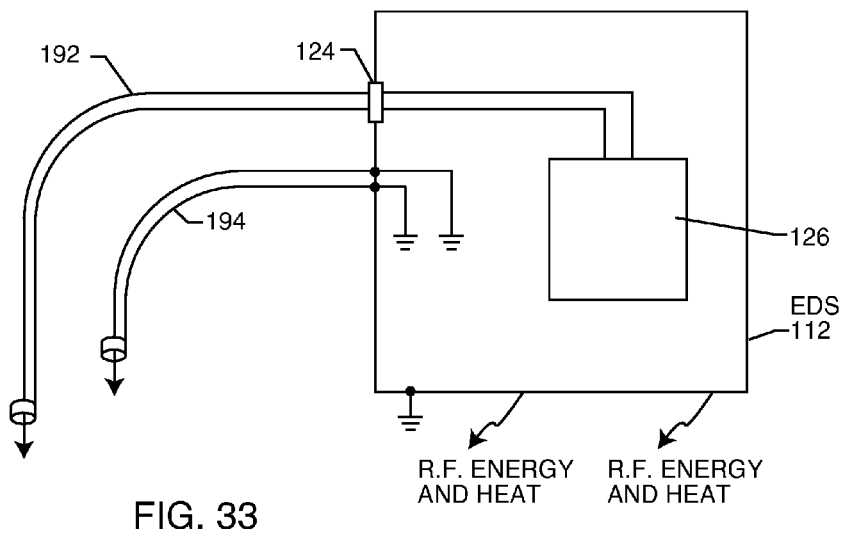
FIG. 33 illustrates a schematic line diagram illustrating some of the principles of the present invention.

FIG. 33 is a schematic line diagram illustrating the principles of the present invention. The active lead and its associated conductors 192 are routed through hermetic seal 124 in turn to AIMD circuit board 126. The abandoned lead conductors 194, in accordance with the present invention, are directly attached to the AIMD housing which acts as an energy dissipating surface.

Figure 34:
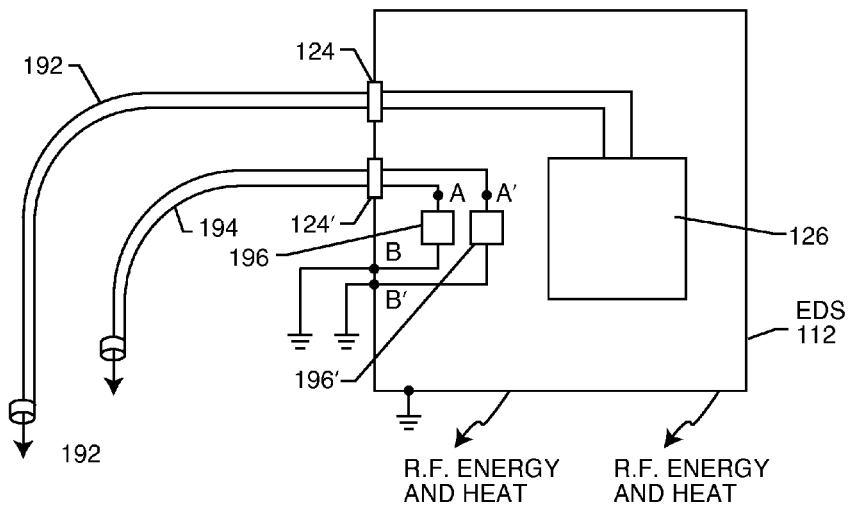
FIG. 34 illustrates an alternative embodiment of the present invention.

FIG. 34 illustrates an alternative embodiment of the present invention. In this case, the abandoned lead conductors 194 are routed through a hermetic seal 124' and in turn to frequency variable diverter elements 196 and 196'. These frequency variable diverter elements are attached to the AIMD housing also known as ground points B and B'. This is so the AIMD housing can act as an energy dissipating surface. Referring once again to FIG. 34, there is a node A which is connectable to an implanted lead conductor and is also connected to one side of the diverter element 196. The other side of the diverter element 196 is connected at node B to the AIMD housing or ground point on the circuit board. In a similar fashion, node A' is connectable to a different implantable lead conductor and also to a second diverter element 196'. The other end of the diverter element 196' is connected to node B' which is also at the electrical potential of the ground of the AIMD housing. Nodes B and B' can be collapsed into a single node at a single point or they can be widely spaced on the AIMD housing. Nodes B and B' can also be different points on a circuit board which was in turn grounded to the AIMD housing. It will be appreciated that any number of nodes A and A' can coincide with any number of abandoned lead conductors. Also, there can be any number of grounding points B as required for the number of abandoned lead conductors.

Figure 35:
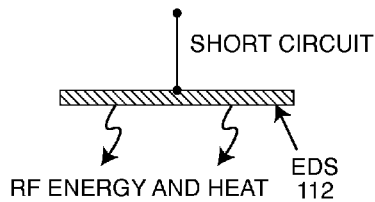
FIG. 35 illustrates an electrical schematic of the short circuit or grounding of the abandoned lead conductor as previously illustrated in FIG. 33.

FIG. 35 is an electrical schematic of the short circuit or grounding of the abandoned lead conductors 194, as previously illustrated in FIG. 33.

Figure 36:
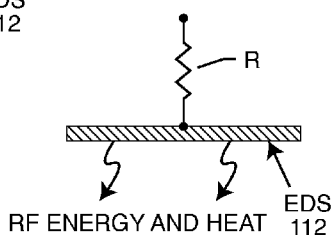
FIG. 36 illustrates that the short circuit will have an inherent resistance R.

FIG. 36 illustrates that the short circuit will have an inherent resistance R.

Figure 37:
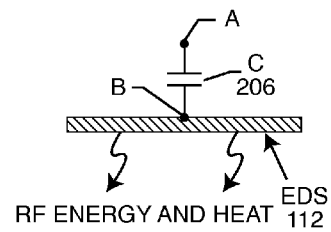
FIG. 37 illustrates that the diverter elements may be a capacitor.

FIG. 37 illustrates that the diverter elements may be a capacitor 206. In this case, an ideal capacitor element is as shown, meaning that it has no inductance and no resistance. A capacitor is an ideal frequency variable diverter because at high frequencies, such at MRI RF-pulsed frequencies, it will tend to look like a very low impedance for a short circuit.

Figure 38:
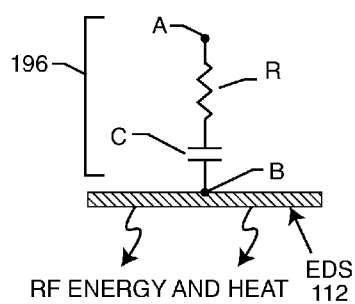
FIG. 38 illustrates one type of frequency variable diverter as previously illustrated in FIG. 34.

FIG. 38 is one type of frequency variable diverter 196 as previously illustrated in FIG. 34. In this case, there is a capacitor C. The resistance r can be a discrete resistor or it can be the inherent resistance of the capacitor which is also known as the capacitor's equivalent series resistance or ESR. At low frequency, the capacitor C as previously illustrated in FIG. 38, will look like a very high impedance. In face, at biological frequencies below one to two kilohertz, the capacitor C will look desirably like an open circuit. However, at high frequency, the capacitor C will tend to look like a short circuit and draw induced MRI RF energy from the lead where it is diverted to the AIMD housing 112 as an energy dissipating surface. These implanted leads are usually coiled and tend to look inductive as a source impedance. In order to transfer maximum energy to the energy dissipating surface, a capacitive element is desirable so that the $+j\Omega L$ term will be canceled by the $-j\Omega C$ term.

Figure 39:
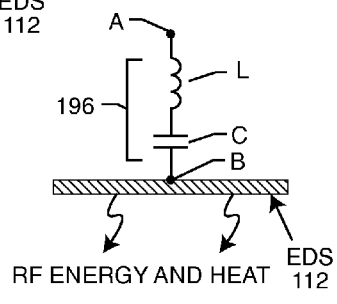
FIG. 39 illustrates a different type of diverter known as an L-C trap.

FIG. 39 illustrates a different type of diverter known as an L-C trap. In this case, the inductor element L and the capacitor element C are designed to be resonant at one or more MRI RF-pulsed frequencies. At resonance, an L-C trap tends to look like a short circuit. Accordingly, in accordance with the present invention, MRI induced RF energy on the abandoned lead, is shorted to the EDS surface 112.

Figure 40:
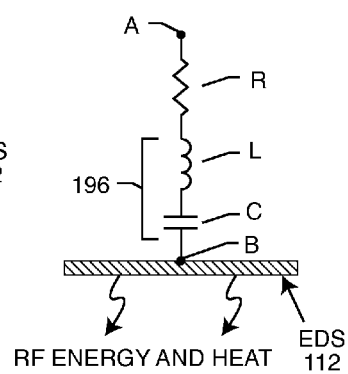
FIG. 40 illustrates the addition of a resistor to the L-C trap of FIG. 39.

FIG. 40 illustrates the addition of a resistor to the L-C trap of FIG. 39. The resistive element is important so one can control the Q and the bandwidth of the L-C trap at resonance. One of these principles is more thoroughly described in U.S. Pat. No. 7,966,075, the contents of which are incorporated herein by reference.

Figure 41:
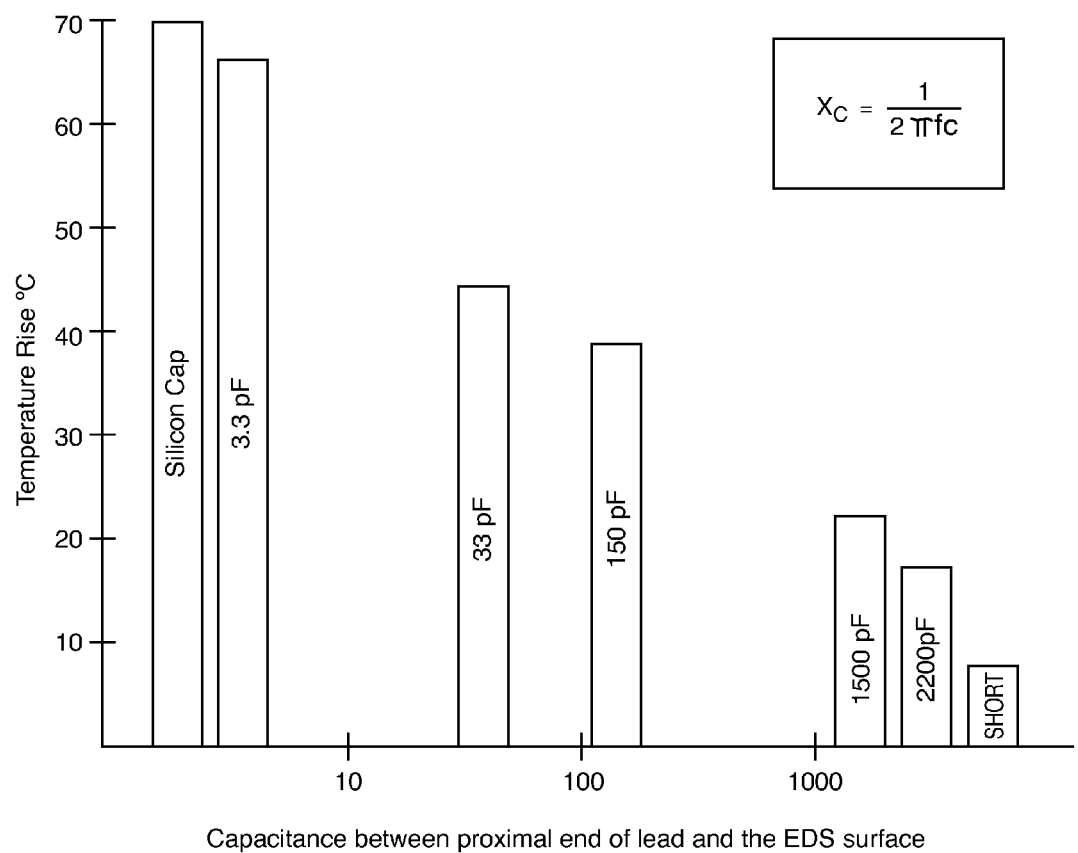
FIG. 41 illustrates a bar graph showing experimental data taken by the inventors with various types of abandoned leads.

FIG. 41 is a bar graph showing experimental data taken by the inventors with various types of abandoned leads. This data was taken in a human body phantom filled with an ASTM gel. Luxtron fiber optic probes were used to make precise temperature measurements of the distal electrodes. The temperature rise in degrees centigrade is shown on the Y axis. The X axis shows different types of proximal abandoned lead end terminations. On the far left, there is a silicone cap abandoned lead as shown which has a 70 degree temperature rise. When added to 37 degrees body temperature, one can see that this is a 107 degrees absolute temperature, which is above the boiling point of water and is extraordinarily dangerous to human tissues. Looking at the far right hand side of the bar graph, one can see that frequency variable diverter capacitors of 1500 and 2200 picofarads are both very effective in reducing the amount of distal tip heating. The best case turned out to be a short to an AIMD housing. Accordingly, the short circuit is the preferred embodiment, in the present invention. The equation shown in FIG. 41 relates to capacitive reactance to the frequency and the capacitance value. Frequency appears as f in the dominator. The capacitance value is shown by C. The capacitive reactance $x_C$ is in ohms, the frequency is in hertz, and the capacitance is in farads. As one can see, with the capacitance appearing in the denominator, for higher capacitance values, capacitive reactance will be lower. This is why the highest capacitance values, 1500 picofarad and 2200 picofarad, act nearly as good as the short circuit.

U.S. patent application Ser. No. 13/413,463 filed on Mar. 6, 2012 entitled SECONDARY HEADER FOR AN IMPLANTABLE MEDICAL DEVICE INCORPORATING AN ISO DF4 CONNECTOR AND CONNECTOR CAVITY AND/OR AN IS4 CONNECTOR AND CONNECTOR CAVITY is fully incorporated herein with this reference.

In review, various embodiments of the present invention include a header for an active implantable medical device includes a header block body. An active connector cavity is located within the header block body and configured to attach to an active lead. A first conductive leadwire is electrically connected to the active connector cavity at one end and at its other end connected to or through a hermetic terminal of the active implantable medical device. An abandoned connector cavity is also located within the header block body and configured to attach to an abandoned lead. A second conductive leadwire is electrically connected to the abandoned connector cavity at one end and at its other end connected to the active implantable medical device housing. An auxiliary header is associated with the header including a header plug configured for mating physical and electrical insertion into the abandoned connector cavity and including at least two auxiliary abandoned connector cavities.

The active connector cavity may include a plurality of active connector cavities. The active connector cavity may include an ISO IS-1, IS4, DF-1 or DF4 connector cavity. The abandoned connector cavity may include an ISO IS-1, IS4, DF-1 or DF4 connector cavity. The abandoned connector cavity may include an ISO DF-1 connector cavity.

A diverter circuit may be electrically connected between the abandoned connector cavity and the active implantable medical device housing. The diverter circuit may include a short, a resistance, a capacitor, an R-C circuit, an L-C circuit or an R-L-C circuit. The second conductive leadwire may include a short to the active implantable medical device housing.

An RFID tag may be affixed to or embedded within the header block body or the lead adapter. U.S. Pat. No. 8,543, 209 issued on Sep. 24, 2013 is incorporated in full herein with this reference. FIG. 47 of the '209 patent shows an RFID chip 220 and RFID antenna 222 embedded in a low profile secondary header (lead adapter) 160. Similarly, an RFID chip/antenna can be embedded in the lead adapters 182 of the present invention. U.S. Pat. No. 8,326,435 issued on Dec. 4, 2012 is incorporated in full herein with this reference. FIG. 1 of the shows an RFID chip 12 embedded in the header body 36. Similarly, the RFID chip can be embedded in the header body 114 of the present invention.

The at least two auxiliary abandoned connector cavities may be electrically coupled to the second conductive leadwire. The auxiliary header may have a low profile conforming shape, including an intermediate conformal section between the header plug and the AIMD housing for placing the at least two auxiliary header connector cavities adjacent to an exterior surface of the AIMD when the auxiliary header plug is placed within the abandoned connector cavity. In some embodiments the auxiliary header may be spaced no more than 2 mm from the AIMD exterior surface. In some embodiments the auxiliary header may have an exterior surface which tightly conforms to an adjacent AIMD exterior surface.

Although several embodiments have been described in detail for purposes of illustration, various modifications may be made to each without departing from the scope and spirit of the invention. Accordingly, the invention is not to be limited, except as by the appended claims.

What is claimed is:

1. A header connector block attachable to a housing of an active implantable medical device, the header connector block comprising:
   a) a header block body;
   b) at least one active connector cavity located within the header block body, wherein the active connector cavity is configured to be electrically connectable to an implantable lead of an active implantable medical device;
   c) at least one abandoned connector cavity located within the header block body, wherein the abandoned connector cavity is configured to be electrically connectable to an abandoned implanted lead;
   d) a first conductive leadwire disposed within the header block body, the first header block leadwire extending from a first leadwire proximal end to a first leadwire distal end, wherein the first header block leadwire distal end is electrically connected to the at least one active connector cavity and the first header block leadwire proximal end is electrically connectable to a conductive feedthrough of a hermetic terminal of an active implantable medical device; and
   e) a second conductive leadwire disposed within the header block body, the second header block leadwire extending from a second leadwire proximal end to a second leadwire distal end, wherein the second header block leadwire distal end is electrically connected to the at least one abandoned connector cavity and the second header block leadwire proximal end is electrically groundable to a housing for the active implantable medical device.

2. The header connector block of claim 1, wherein the at least one active connector cavity comprises a plurality of active connector cavities, each active connector cavity being electrically connected to at least one first header block leadwire distal end of a respective one of a plurality of first header block leadwires.

3. The header connector block of claim 1, wherein the at least one active connector cavity is selected from the group consisting of an ISO IS-1 connector cavity, an IS4 connector cavity, a DF-1 connector cavity, and a DF4 connector cavity.

4. The header connector block of claim 1, wherein the at least one abandoned connector cavity is selected from the group consisting of an ISO IS-1 connector cavity, an IS4 connector cavity, a DF-1 connector cavity, and a DF4 connector cavity.

5. The header connector block of claim 1, wherein the at least one abandoned connector cavity comprises an ISO DF-1 connector cavity.

6. The header connector block of claim 1, wherein the second header block leadwire is configured to electrically short an abandoned implanted lead connected to the abandoned connector cavity to the active implantable medical device housing.

7. The header connector block of claim 1, including a lead adapter comprising an adapter plug end configured to be physically inserted into and electrically coupled to the at least one abandoned connector cavity.

8. The header connector block of claim 7, including an RFID tag affixed to or embedded within the header block body or the lead adapter.

9. The header connector block of claim 7, wherein the lead adapter comprises at least two auxiliary abandoned connector cavities, and wherein when the adapter plug end is inserted into and electrically coupled to the at least one abandoned connector cavity, the at least two auxiliary abandoned connector cavities are electrically groundable to the housing for the medical device through the second header block leadwire.

10. The header connector block of claim 9, wherein the at least two auxiliary abandoned connector cavities are respectively selected from the group consisting of an ISO IS-1 connector cavity, an IS4 connector cavity, a DF-1 connector cavity, and a DF4 connector cavity.

11. The header connector block of claim 9, wherein the lead adapter has a low profile conforming shape configured for placing the at least two auxiliary abandoned connector cavities adjacent to an exterior surface of an implantable medical device when the adapter plug end is physically inserted into and electrically coupled to the at least one abandoned connector cavity.

12. The header connector block of claim 11, wherein the lead adapter is spaced no more than 2 mm from an exterior surface of an implantable medical device when the adapter plug end is physically inserted into and electrically coupled to the at least one abandoned connector cavity.

13. The header connector block of claim 11, wherein the lead adapter is configured to have an exterior surface that tightly conforms to an adjacent exterior surface of an implantable medical device when the adapter plug end is physically inserted into and electrically coupled to the at least one abandoned connector cavity.

14. The header connector block of claim 1, wherein the header block body comprises a threaded connector block that is electrically groundable to the device housing and wherein with an abandoned implanted lead connected to the at least one abandoned connector cavity, a set screw is threadable into the threaded connector block and into contact with the abandoned lead to thereby complete electrical grounding of the abandoned lead to the housing for the medical device.

15. An active implantable medical device, comprising:
a) an active implantable medical device housing including a hermetic terminal, the hermetic terminal comprising:
   i) a hermetic seal supported by and electrically coupled to the device housing; and
   ii) a conductive feedthrough passing through the hermetic seal so that the conductive feedthrough is in a non-conductive relation with the device housing; and
b) a header block body attached to the device housing;
c) at least one active connector cavity located within the header block body, wherein the active connector cavity is configured to be electrically connectable to an implantable lead of an active implantable medical device;
d) at least one abandoned connector cavity located within the header block body, wherein the abandoned connector cavity is configured to be connectable to an abandoned implanted lead;
e) a first conductive leadwire disposed within the header block body, the first header block leadwire extending from a first leadwire proximal end to a first leadwire distal end, wherein the first header block leadwire distal end is electrically connected to the at least one active connector cavity and the first header block leadwire proximal end is electrically connected to the at least one conductive feedthrough of the hermetic terminal; and
f) a second conductive leadwire disposed within the header block body, the second header block leadwire extending from a second leadwire proximal end to a second leadwire distal end, wherein the second header block leadwire distal end is electrically connected to the abandoned connector cavity and the second header block leadwire proximal end is electrically groundable to the hermetic seal or to the housing for the medical device.

16. The active implantable medical device of claim 15, wherein the header block body comprises a threaded connector block that is electrically grounded to the device housing and wherein with an abandoned implanted lead connected to the at least one abandoned connector cavity, a set screw is threadable into the threaded connector block and into contact with the abandoned lead to thereby complete electrical grounding of the abandoned lead to the housing for the medical device.

17. An active implantable medical device, comprising:
a) an active implantable medical device housing including at least one hermetic terminal, the hermetic terminal comprising:
   i) a hermetic seal supported by and electrically coupled to the device housing; and
   ii) at least two conductive feedthrough passing through the hermetic seal so that the conductive feedthroughs are in a non-conductive relation with the device housing; and
b) a header block body attached to the device housing;
c) at least one active connector cavity located within the header block body, wherein the active connector cavity is configured to be electrically connectable to an implantable lead of an active implantable medical device;
d) at least one abandoned connector cavity located within the header block body, wherein the abandoned connector cavity is configured to be connectable to an abandoned implanted lead;
e) a first conductive leadwire disposed within the header block body, the first header block leadwire extending from a first leadwire proximal end to a first leadwire distal end, wherein the first header block leadwire distal end is electrically connected to the at least one active connector cavity and the first header block leadwire proximal end is electrically connected to a first one of the conductive feedthroughs of the hermetic terminal;
f) a second conductive leadwire disposed within the header block body, the second header block leadwire extending from a second leadwire proximal end to a second leadwire distal end, wherein the second header block leadwire distal end is electrically connected to the at least one abandoned connector cavity and the second header block leadwire proximal end is electrically connected to a second one of the conductive feedthroughs of the hermetic terminal; and g) a diverter circuit disposed inside the device housing, the diverter circuit comprising a diverter circuit first end and a diverter circuit second end, wherein the diverter circuit first end is electrically switchable between the first and second conductive feedthroughs of the hermetic terminal and the diverter circuit second end is electrically grounded to the device housing.

18. The active implantable medical device of claim 17, wherein the diverter circuit is selected from the group consisting of a resistance, a capacitor, an R-C circuit, an L-C circuit, and an R-L-C circuit.

19. The active implantable medical device of claim 17, wherein the at least one abandoned connector cavity comprises an ISO DF-1 connector cavity.

20. An abandoned implanted lead header attachable to an active implantable medical device housing, the abandoned implanted lead header comprising:
  a) a header block body;
  b) at least one abandoned connector cavity located within the header block body, wherein the abandoned connector cavity is configured to be electrically connectable to an abandoned implanted lead;
  c) a conductive clip attached to the header block body, wherein the conductive clip is configured to tightly slip onto a housing for an implantable medical device; and
  d) a conductive leadwire disposed within the header block body, the header block leadwire extending from a leadwire proximal end to a leadwire distal end, wherein the header block leadwire distal end is electrically connected to the at least one abandoned connector cavity and the header block leadwire proximal end is electrically connected to the conductive clip,
  e) so that when an abandoned lead is electrically connected to the abandoned connector cavity in the header block body and the conductive clip is attached to the device housing, the header block leadwire proximal end electrically connected to the conducive clip provides for shunting of MRI RF energy from the abandoned lead to the device housing.

21. The abandoned implanted lead header of claim 20, wherein the at least one abandoned connector cavity is selected from the group consisting of an ISO IS-1 connector cavity, an IS4 connector cavity, a DF-1 connector cavity, and a DF4 connector cavity.

* * * * *